United States Patent
Momose

(10) Patent No.: US 9,492,609 B2
(45) Date of Patent: Nov. 15, 2016

(54) LIQUID TRANSPORT DEVICE

(71) Applicant: SEIKO EPSON CORPORATION, Tokyo (JP)

(72) Inventor: Yoshihiko Momose, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 14/639,891

(22) Filed: Mar. 5, 2015

(65) Prior Publication Data

US 2015/0250942 A1 Sep. 10, 2015

(30) Foreign Application Priority Data

Mar. 7, 2014 (JP) ................ 2014-044767
Mar. 7, 2014 (JP) ................ 2014-044768

(51) Int. Cl.
*A61M 5/142* (2006.01)
*A61M 5/158* (2006.01)

(52) U.S. Cl.
CPC ..... *A61M 5/14248* (2013.01); *A61M 5/14228* (2013.01); *A61M 2005/14252* (2013.01); *A61M 2005/14264* (2013.01); *A61M 2005/14268* (2013.01); *A61M 2005/1586* (2013.01); *A61M 2205/121* (2013.01); *A61M 2205/123* (2013.01); *A61M 2205/125* (2013.01); *A61M 2205/7536* (2013.01); *A61M 2209/045* (2013.01)

(58) Field of Classification Search
CPC .............. A61B 2560/0412; A61B 5/6833; A61M 5/14248; A61M 2005/14268; A61M 5/14244; A61M 5/15224; A61M 5/1424
USPC ................. 604/131–155, 180, 539
See application file for complete search history.

(56) References Cited

U.S. PATENT DOCUMENTS

| | | | |
|---|---|---|---|
| 5,858,001 A | 1/1999 | Tsals et al. | |
| 5,968,011 A * | 10/1999 | Larsen | A61M 5/158 604/164.01 |
| 2004/0116865 A1* | 6/2004 | Bengtsson | A61M 5/14248 604/171 |
| 2005/0065472 A1* | 3/2005 | Cindrich | A61M 5/14248 604/134 |

(Continued)

FOREIGN PATENT DOCUMENTS

| | | |
|---|---|---|
| DE | 696 20 257 T2 | 11/2002 |
| JP | 2002-505600 A | 2/2002 |

(Continued)

OTHER PUBLICATIONS

Partial European Search Report dated Jul. 31, 2015 as received in Application No. 15157751.7.

(Continued)

*Primary Examiner* — Gerald Landry, II
(74) *Attorney, Agent, or Firm* — Maschoff Brennan

(57) ABSTRACT

A liquid transport device is attachable to a living body and transports a liquid to the living body. The liquid transport device includes a pump unit that includes a storage portion for storing the liquid and a pumping portion for transporting the liquid in the storage portion to the living body, and a seal portion that attaches the pump unit to the living body. A portion of a surface of the living body side of the pump unit is separated from an upper surface of the seal portion. In the liquid transport device, the pump unit is easily fixed to a flexible surface of the living body and a load on the living body is reduced while securing areas for the lower surface of the pump unit and the sealing surface of the seal portion.

12 Claims, 16 Drawing Sheets

(56) References Cited

U.S. PATENT DOCUMENTS

| | | | |
|---|---|---|---|
| 2005/0215979 A1 | 9/2005 | Kornerup et al. | |
| 2005/0277882 A1 | 12/2005 | Kriesel | |
| 2007/0078393 A1* | 4/2007 | Lynch | A61M 5/14244 604/131 |
| 2007/0154336 A1 | 7/2007 | Miyazaki et al. | |
| 2009/0069750 A1* | 3/2009 | Schraga | A61M 5/14248 604/167.02 |
| 2009/0088682 A1* | 4/2009 | Cross | A61M 5/14248 604/38 |
| 2009/0259209 A1* | 10/2009 | Chong | A61M 5/14248 604/403 |
| 2009/0326454 A1* | 12/2009 | Cross | A61M 5/1424 604/151 |
| 2010/0004596 A1 | 1/2010 | De Polo | |
| 2010/0016791 A1* | 1/2010 | Chong | A61M 5/002 604/93.01 |
| 2010/0121306 A1* | 5/2010 | Yodfat | A61B 5/14532 604/500 |
| 2010/0179473 A1* | 7/2010 | Genosar | A61M 5/14248 604/70 |
| 2010/0204657 A1* | 8/2010 | Yodfat | A61M 5/14248 604/181 |
| 2011/0186143 A1* | 8/2011 | Miyazaki | A61M 5/14228 137/67 |
| 2012/0209240 A1* | 8/2012 | Gray | G05D 7/0647 604/500 |
| 2014/0107580 A1 | 4/2014 | Momose | |

FOREIGN PATENT DOCUMENTS

| | | |
|---|---|---|
| JP | 2007-530105 A | 11/2007 |
| JP | 2010-534085 A | 11/2010 |
| WO | 96/37244 A1 | 11/1996 |
| WO | 2004/105839 A1 | 12/2004 |
| WO | 2007/074363 A2 | 7/2007 |
| WO | 2008/080990 A1 | 7/2008 |
| WO | 2009/016637 A2 | 2/2009 |

OTHER PUBLICATIONS

Extended European Search Report dated Nov. 19, 2015 as received in Application No. 15 15 7751.

* cited by examiner

LIQUID TRANSPORT DEVICE

BACKGROUND

1. Technical Field

The present invention relates to a liquid transport device.

2. Related Art

A device disclosed in JP-T-2010-534085 has been known as a liquid transport device for transporting a liquid to a living body. In the liquid transport device, a liquid of a liquid storage portion is injected into the living body by driving a pump while puncturing the living body with an injection portion (a catheter or the like) which injects the liquid.

JP-T-2010-534085 discloses that a dosage patch unit is connected on a frame unit which is attached to a patient's skin (the surface of a living body).

JP-T-2010-534085 discloses that since a sealing surface is fixed to the entire lower surface of the dosage patch unit via the frame unit, the sealing surface disclosed in JP-T-2010-534085 is formed into a wide and solid planar shape. As a result, the liquid transport device is easily detached from a flexible surface of the living body, and the surface of the living body is corrected to be a planar surface by the flat sealing surface, thereby increasing a load (pain) on the living body.

On the other hand, like the dosage patch unit disclosed in JP-T-2010-534085, a unit (a pump unit) which accommodates the liquid storage portion (the storage portion) and the pump needs to be a certain size, and thus there is a limitation to the reduction of an area of a lower surface of the unit. In addition, the sealing surface also needs an area such that the liquid transport device is fixed to the surface of the living body, and thus there is a limitation to the reduction of the sealing surface.

SUMMARY

An advantage of some aspects of the invention is to provide a device capable of being easily fixed to a flexible surface of the living body and reducing a load on the living body while ensuring areas of a lower surface of a pump unit and a sealing surface of a seal portion.

An aspect of the invention is directed to a liquid transport device which is attachable to a living body and transports a liquid to the living body, the device including a pump unit that includes a storage portion for storing the liquid and a pumping portion for transporting the liquid in the storage portion to the living body; and a seal portion that attaches the pump unit to the living body, in which a portion of a surface of the living body side of the pump unit is separated from an upper surface of the seal portion.

Other features of the invention will become clear through the description of the present specification and the accompanying drawings.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1A:
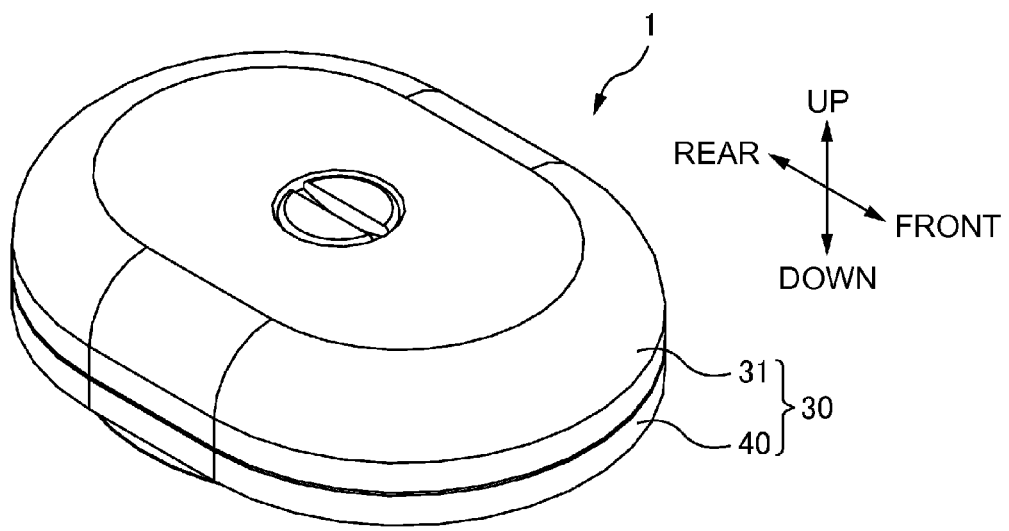
FIGS. 1A and 1B are overall perspective views of a liquid transport device.

At the minimum, the following matters will be made clear by description of the present specification and accompanying drawings.

A liquid transport device which is attachable to a living body and transports a liquid to the living body includes a pump unit that includes a storage portion storing the liquid and a pumping portion for transporting the liquid in the storage portion to the living body; and a seal portion that attaches the pump unit to the living body, in which a portion of a surface of the living body side of the pump unit is separated from an upper surface of the seal portion. Accordingly, the liquid transport device is easily fixed to the flexible surface of the living body and reduces a load on the living body while maintaining areas of the lower surface of the pump unit and the sealing surface of a seal portion.

It is preferable that a portion of the surface of the living body side of the pump unit protrudes in a direction along the surface of the living body from the seal portion. Accordingly, it is possible to form the seal portion to be smaller than the lower surface of the pump unit.

It is preferable that the pump unit is detachably provided to an injection set including the seal portion. Accordingly, it is convenient that the pump unit can be detached in a state in which the injection set is attached to the living body.

It is preferable that the seal portion is disposed on the periphery of an injection portion for injecting the liquid which is transported by the pump unit to the living body. Accordingly, the injection portion is not easily detached.

It is preferable that the pump unit is detachably provided with respect to the injection set which includes the seal portion and the injection portion, the injection set includes a pedestal portion supporting the pump unit, and the seal portion which is positioned under the pedestal portion is disposed on the periphery of the injection portion. Accordingly, the surface of the living body does not easily move at the periphery of the injection portion, thereby reducing a load on the living body from the injection portion.

The liquid transport device which is attachable to a living body and transports a liquid to the living body includes a storage portion for storing the liquid and a pumping portion for transporting the liquid in the storage portion to the living body, in which the storage portion is formed into a circular arc shape having a width, and a discharge port for discharging the liquid of the storage portion to the pump unit is disposed at one end of the storage portion having a circular arc shape. According to such a liquid transport device, the liquid is not likely to remain in the storage portion and thus the liquid can be efficiently used.

It is preferable that the discharge port is disposed at a position which is closer to the inner periphery which swells inside and has the circular arc shape than the outer periphery which swells outside and has the circular arc shape. Accordingly, it is more difficult for the liquid to remain in the storage portion.

It is preferable that an injection port for injecting the liquid into the storage portion is disposed at the other end which is on the side opposite to the one end at which the discharge port of the storage portion formed into the circular arc shape is provided. Accordingly, it is easy to discharge the gas in the storage portion at the time of injecting the liquid.

It is preferable that the injection port is disposed at a position which is closer to the outer periphery than the inner periphery. Accordingly, the liquid enters into the respective regions of the storage portion in order at the time of injecting the liquid and thus the gas is not likely to remain in the storage portion.

It is preferable that the curvature of the outer periphery is smaller than the curvature of the inner periphery. Accordingly, since the liquid in the storage portion passes through the vicinity of an inner periphery as a flow path and then is discharged from a discharge port, the liquid is not likely to remain in the storage portion at the time of being discharged.

It is preferable that the width in the center portion of the storage portion is greater than the width in the end portion of the storage portion. Accordingly, it is possible to increase the capacity of the storage portion.

It is preferable that a liquid feeding port for sending the liquid transported by the pump unit to the outside is included and a filter is provided in the liquid feeding port, which allows a gas to pass through but does not allow the liquid to pass through at the time of injecting the liquid into the storage portion. Accordingly, at the time of injecting the liquid, it is possible to prevent the liquid from leaking to the outside while discharging the gas in the flow path to the outside.

First Embodiment

Outline of Liquid Transport Device 1

Figure 1B:
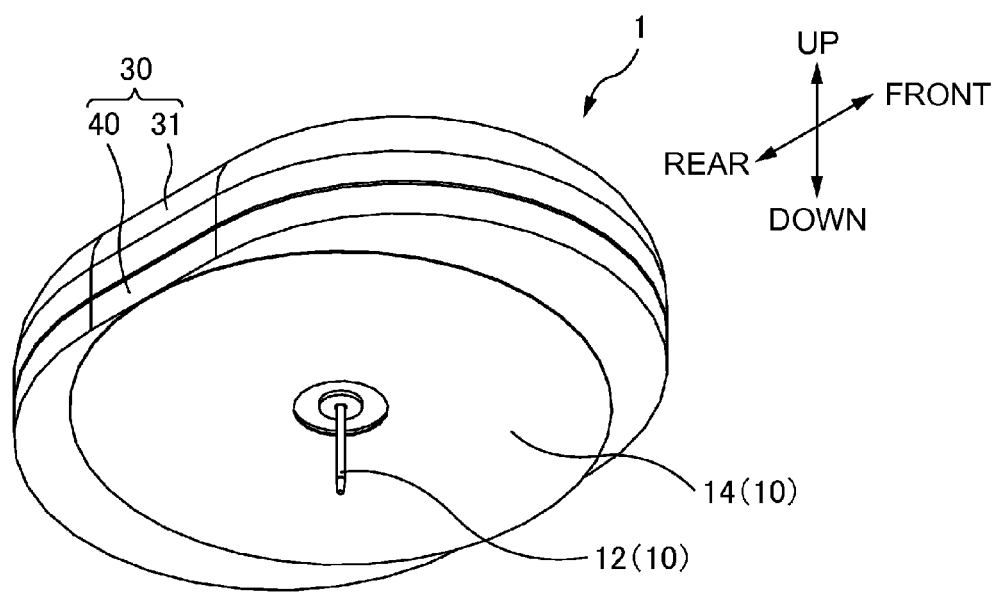
Figure 2:
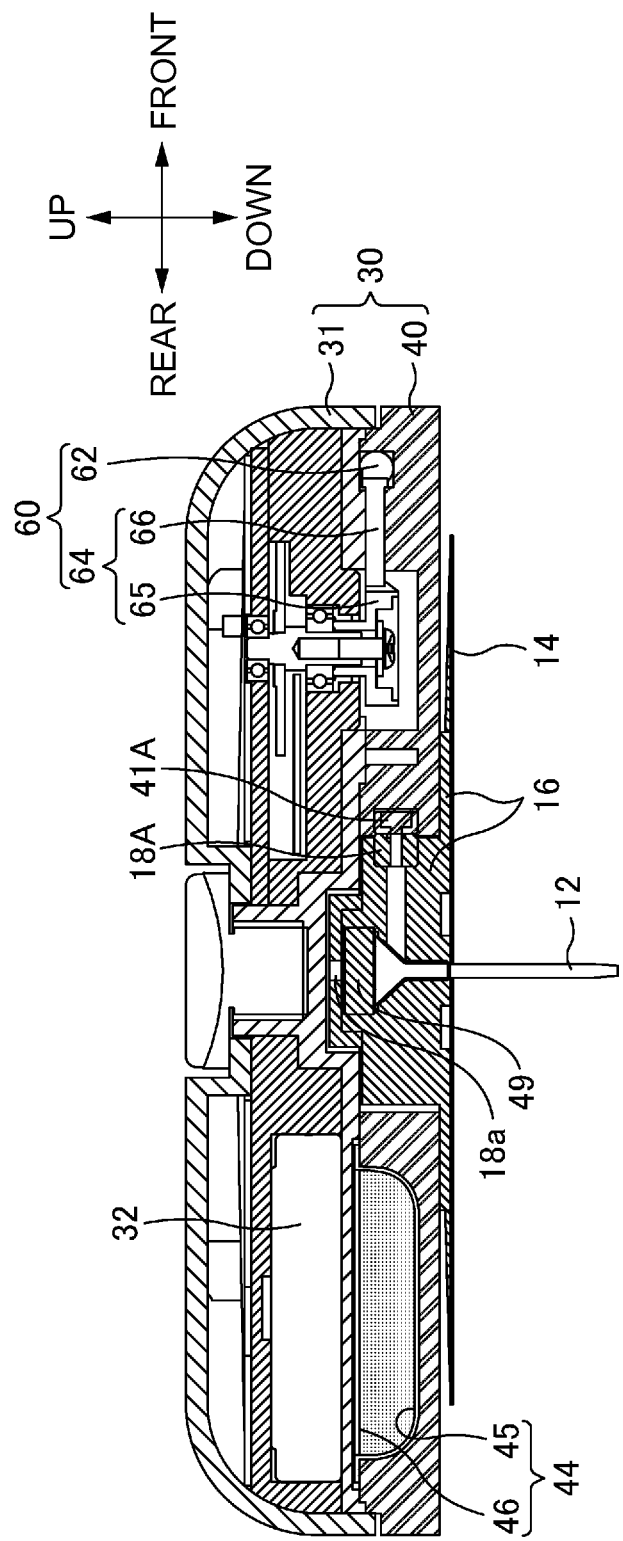
FIG. 2 is a cross-sectional view of the liquid transport device.
Figure 3A:
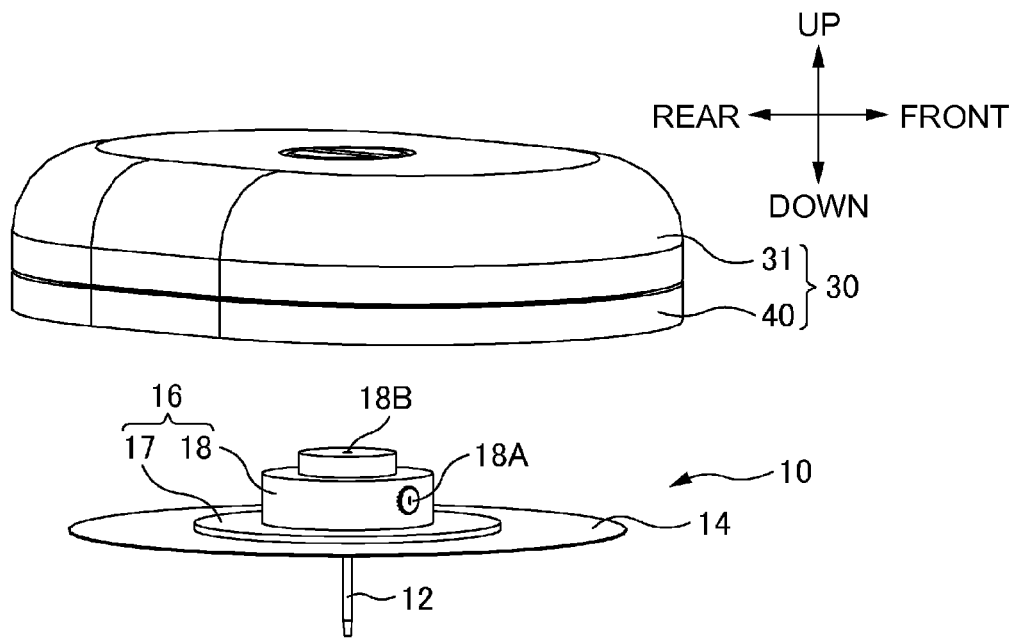
FIGS. 3A and 3B are exploded views of the liquid transport device.
Figure 3B:
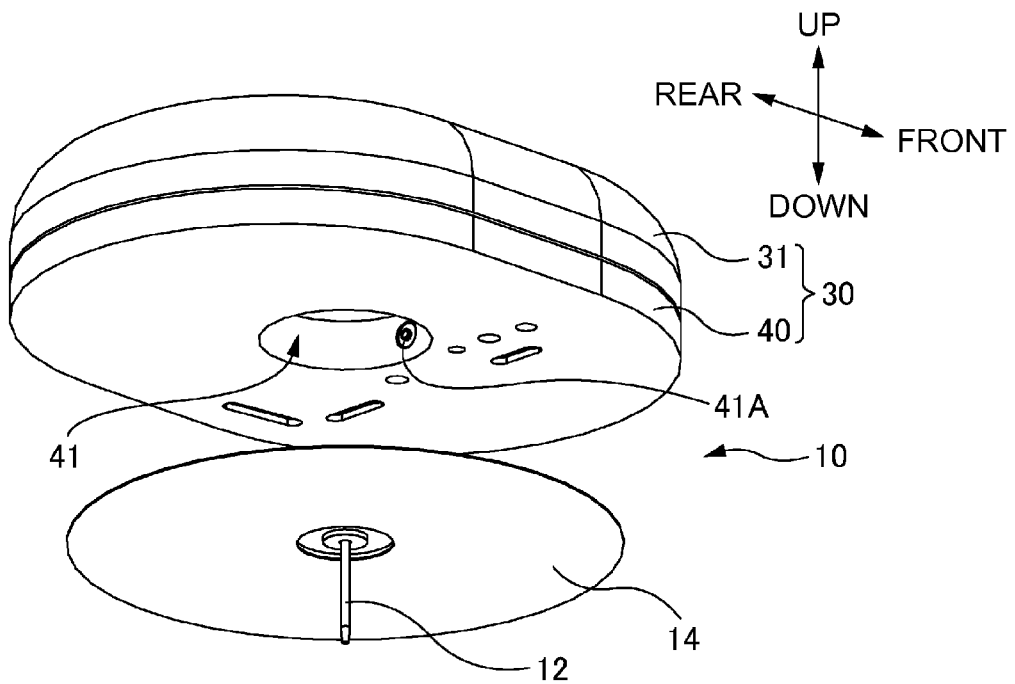

FIGS. 1A and 1B are overall perspective views of a liquid transport device 1. FIG. 2 is a cross-sectional view of the liquid transport device 1. FIGS. 3A and 3B are exploded views of the liquid transport device 1. In the following description, the side to which the liquid transport device 1 is attached (the living body side) is assumed to be "lower" and the opposite side is assumed to be "upper". In addition, as illustrated in FIG. 2, a side on which a pumping portion 60 is provided with respect to a catheter 12 is assumed to be "front" and a side on which a reservoir 44 which stores the liquid is provided is assumed to be "rear".

The liquid transport device 1 is a device for transporting the liquid. The liquid transport device 1 includes an injection set 10 and a pump unit 30. The injection set 10 and the pump unit 30 can be separated from each other as illustrated in FIGS. 3A and 3B, but are integrally assembled when being used as illustrated in FIGS. 1A and 1B. The liquid transport device 1 is preferably used to, for example, periodically inject insulin which is stored in the pump unit 30 and attaches the injection set 10 to the living body.

A connection portion 18 which protrudes upward is provided on the injection set 10. A hollow receiving portion 41 is provided in the center of the lower surface of the pump unit 30. The pump unit 30 is attached to the injection set 10 by inserting the connection portion 18 of the injection set 10 into the receiving portion 41 of the pump unit 30. At this time, a liquid receiving port 18A on the side surface of the connection portion 18 is connected to a liquid feeding port 41A of the receiving portion 41. The reservoir 44 and a pumping portion 60 are provided on the pump unit 30 as will be described later. The liquid of the reservoir 44 is sent from the liquid feeding port 41A to the injection set 10 by the pumping portion 60 and then injected to the living body from a catheter 12 of the injection set 10.

Configuration of Injection Set 10

The injection set 10 is a part for injecting the liquid to the living body. As illustrated in FIGS. 3A and 3B, the injection set 10 includes the catheter 12, a seal portion 14, and a pedestal portion 16.

The catheter 12 is a tube for injecting the liquid into the living body. The catheter 12 is referred to as "cannula", "cannulae", or "soft needle (soft cannula)" in some cases. The catheter 12 is formed of a soft material, for example, fluororesin or the like. One end of the catheter 12 is fixed to the pedestal portion 16.

The seal portion 14 is a part for attaching the injection set 10 to the living body or the like. The seal portion 14 is, for example, an adhesive pad of which the lower surface is formed of an adhesive seal.

The pedestal portion 16 is a part for attaching the pump unit 30 to the living body. The pedestal portion 16 includes a base portion 17 and a connection portion 18. The base portion 17 is a part for supporting the pump unit 30 from the lower side. The connection portion 18 is a part protruding upward from the base portion 17 and a part which is inserted into the receiving portion 41 of the pump unit 30 (refer to FIG. 3B). The liquid receiving port 18A which is connected to the liquid feeding port 41A is provided on the side surface of the connection portion 18. In addition, an insertion port 18B of an introduction needle 21 (described later) is provided on the upper surface of the connection portion 18.

Figure 4A:
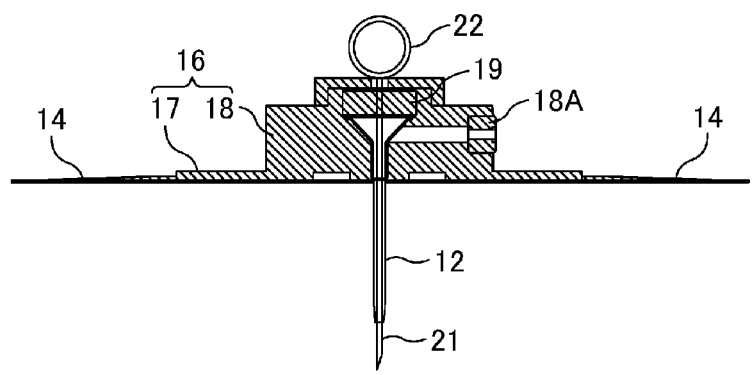
FIGS. 4A and 4B are explanatory diagrams of cross sections of an injection set before and after being attached to a living body.
Figure 4B:
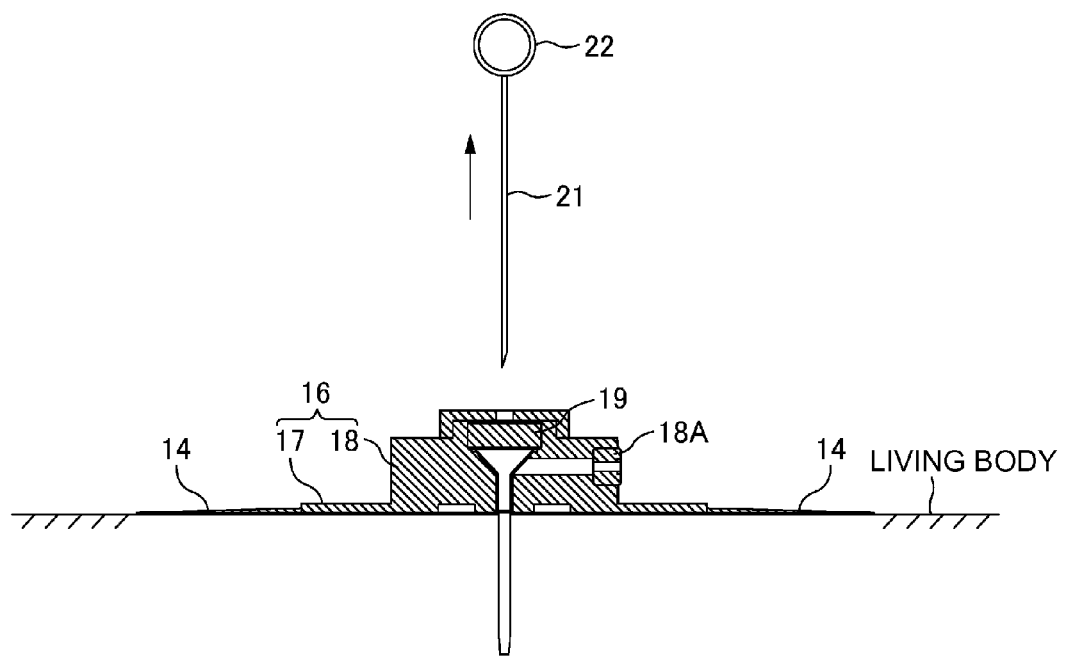

FIGS. 4A and 4B are explanatory diagrams of cross sections of an injection set 10 before and after being attached to a living body.

FIG. 4A is an explanatory diagram of a cross section of an injection set 10 before and after being attached to the living body. In this state, the introduction needle 21 is attached to the injection set 10, the introduction needle 21 pierces through the catheter 12, the seal portion 14, and the pedestal portion 16. An upper end of the introduction needle 21 is fixed to a knob 22. The knob 22 protruding from the upper surface of the connection portion 18 obstructs the mounting of the pump unit 30 in this stage.

When the injection set 10 is attached to the living body, the user punctures the living body with the catheter 12 together with the introduction needle 21. Thereafter, as illustrated in FIG. 4B, the user takes the knob 22 of the introduction needle 21 to pull out (extract) the introduction needle 21 from the injection set 10. The catheter 12 remains in the living body, but since the catheter 12 is soft, the load on the living body is small. A septum for introduction needle 19 is provided on the lower side of the insertion port 18B, which is formed from a material (for example, rubber, silicon, or the like) blocking a hole generated when pulling out the introduction needle 21.

After pulling out the introduction needle 21 from the injection set 10, the pump unit 30 is attached to the injection set 10.

Configuration of Pump Unit 30

Figure 5A:
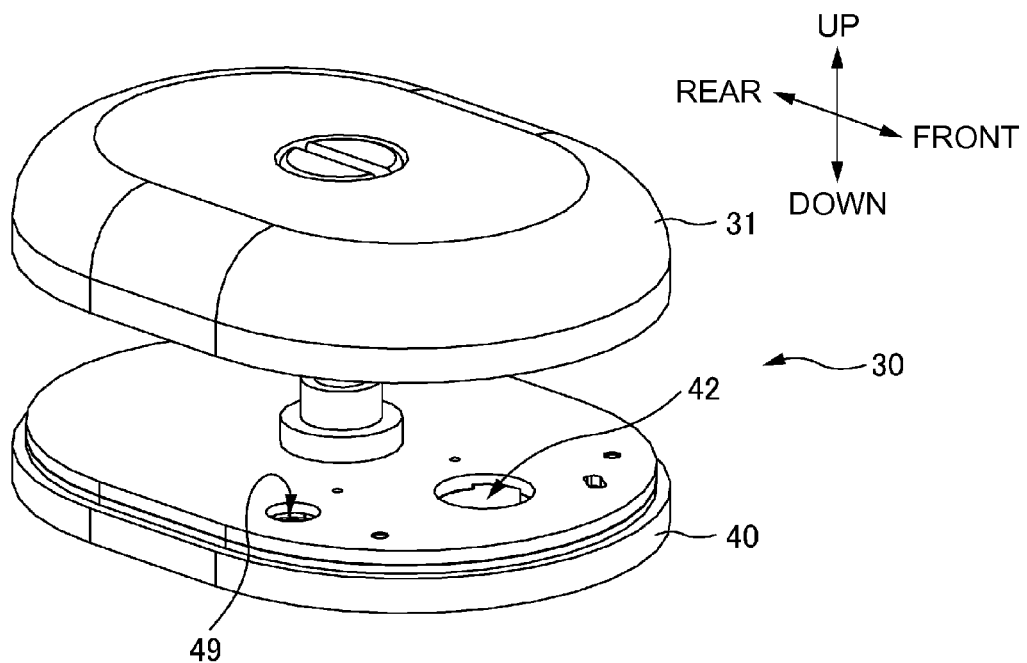
FIGS. 5A and 5B are exploded views of a pump unit.
Figure 5B:
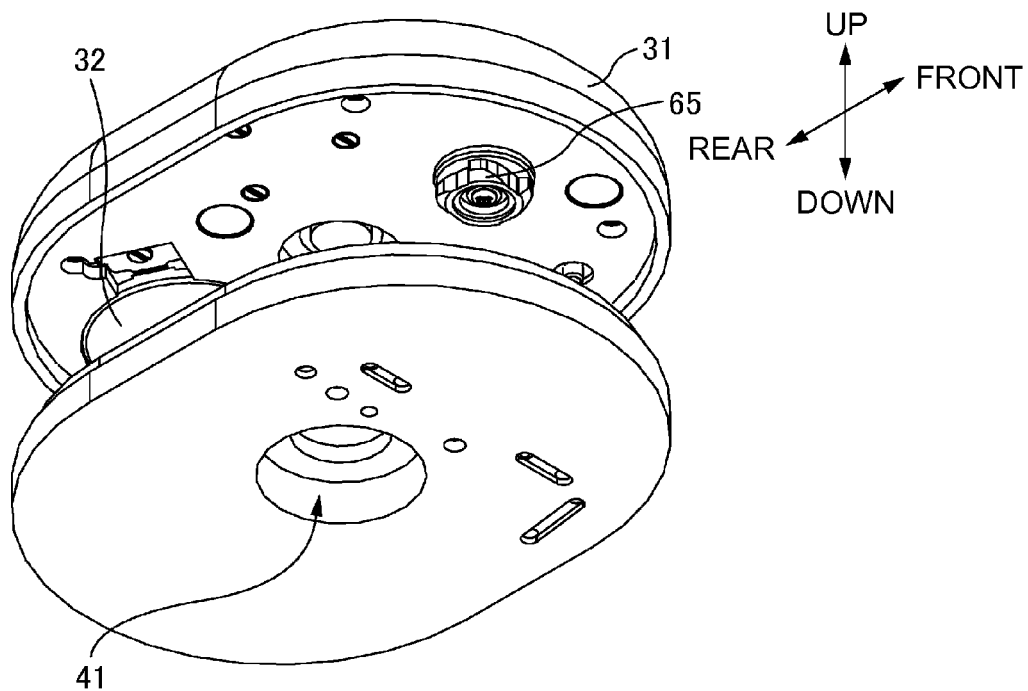

FIGS. 5A and 5B are exploded views of the pump unit 30. The pump unit 30 includes a driving unit 31 and a cartridge 40. The driving unit 31 is fixed to the upper side of the cartridge 40 by a screw.

The driving unit 31 is a component for driving a cam 65. The cam 65 is exposed from the lower side of the driving unit 31 and a driving mechanism (not shown) driving the cam 65 is accommodated inside of the driving unit 31. The driving unit 31 accommodates a battery 32 serving as a source of power, and the battery 32 may be disposed on the cartridge 40 side.

The cartridge 40 includes a cam accommodation portion 42 as illustrated in FIG. 5A. The cam accommodation portion 42 is provided on the upper side of the cartridge 40 (the driving unit 31 side), and is a part which is formed into a hollow shape and accommodates the cam 65 of the driving unit 31. A plurality of fingers 66 (refer to FIG. 6) are disposed on the periphery of the cam accommodation portion 42. When the driving unit 31 is fixed to the cartridge 40, the cam 65 is fitted into the cam accommodation portion 42, thereby the pumping portion 60 to be described next is configured.

Pumping Portion 60

Figure 6:
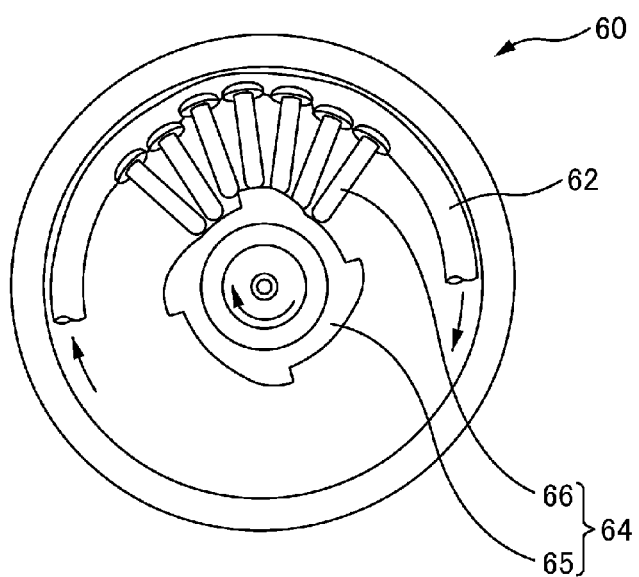
FIG. 6 is an overview diagram of a pumping portion.
Figure 7:
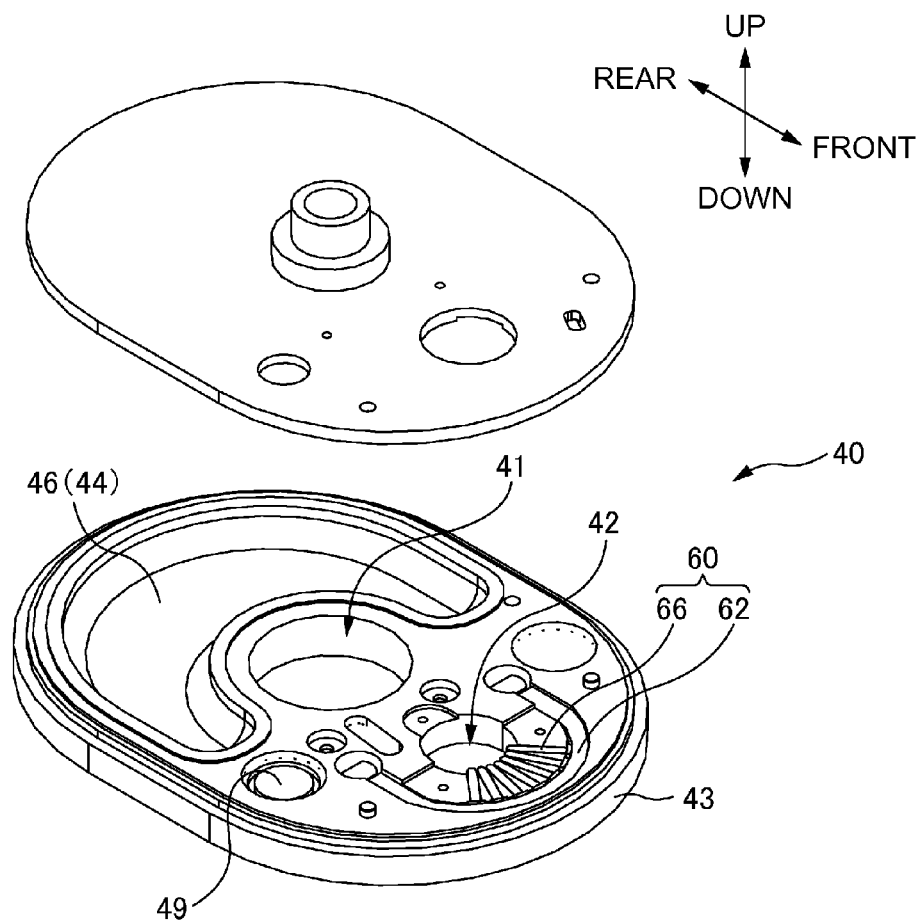
FIG. 7 is an exploded view of a cartridge.

FIG. 6 is an overview diagram of the pumping portion 60. FIG. 7 is an exploded view of the cartridge 40. The pumping portion 60 is apart serving as a pump for transporting the liquid. The pumping portion 60 includes a tube 62 and a compression mechanism 64. The compression mechanism 64 compresses the tube 62, thereby transporting the liquid. The compression mechanism 64 includes a plurality of the fingers 66 and the cam 65.

The tube 62 is a tube for transporting the liquid. The upstream side of the tube 62 (the upstream side when based on the transport direction of the liquid) communicates with the reservoir 44 (refer to FIG. 2) storing the liquid. The downstream side of the tube 62 communicates with the liquid feeding port 41A (refer to FIG. 2 and FIG. 3B). The tube 62 is blocked when being pressed by a finger 66 and has elasticity to the extent of being restored to its original condition when the power is released from the finger 66. The tube 62 is partially formed into a circular arc shape. The center of an arc of the tube 62 matches a rotation center of the cam 65.

The finger 66 is a member blocking the tube 62. The finger 66 is movably supported along an axial direction and is passively moved by receiving power from the cam 65. The plurality of fingers 66 are radially disposed from the rotation center of the cam 65 at equal intervals. The plurality of fingers 66 are disposed between the cam 65 and the tube 62.

The cam 65 includes projection portions on four places on the outer circumference thereof. The plurality of fingers 66 are disposed on the outer circumference of the cam 65, and the tube 62 is provided on the outside of the finger 66. When the cam 65 rotates, seven fingers 66 are sequentially pressed by the projection portion, and the tube 62 is sequentially blocked from the upstream side in the transport direction. When the finger 66 is far from the projection portion, the shape of the tube 62 is restored to the original condition by an elastic force of the tube 62. Accordingly, the tube 62 is caused to perform peristaltic movement, and then the tube 62 is compressed to transport the liquid. In order to prevent the liquid from flowing backward, the projection portion of the cam 65 is formed such that at least one or preferably two fingers 66 block the tube 62.

In the embodiment, in components of the pumping portion 60, the cam 65 is disposed on the driving unit 31, and the tube 62 and the finger 66 are disposed on the cartridge 40. Here, all components of the pumping portion 60 may be disposed on the driving unit 31 or the cartridge 40. In addition, the cam 65 and the finger 66 may be disposed on the driving unit 31 and the tube 62 may be disposed on the cartridge 40.

Reservoir 44

Figure 8A:
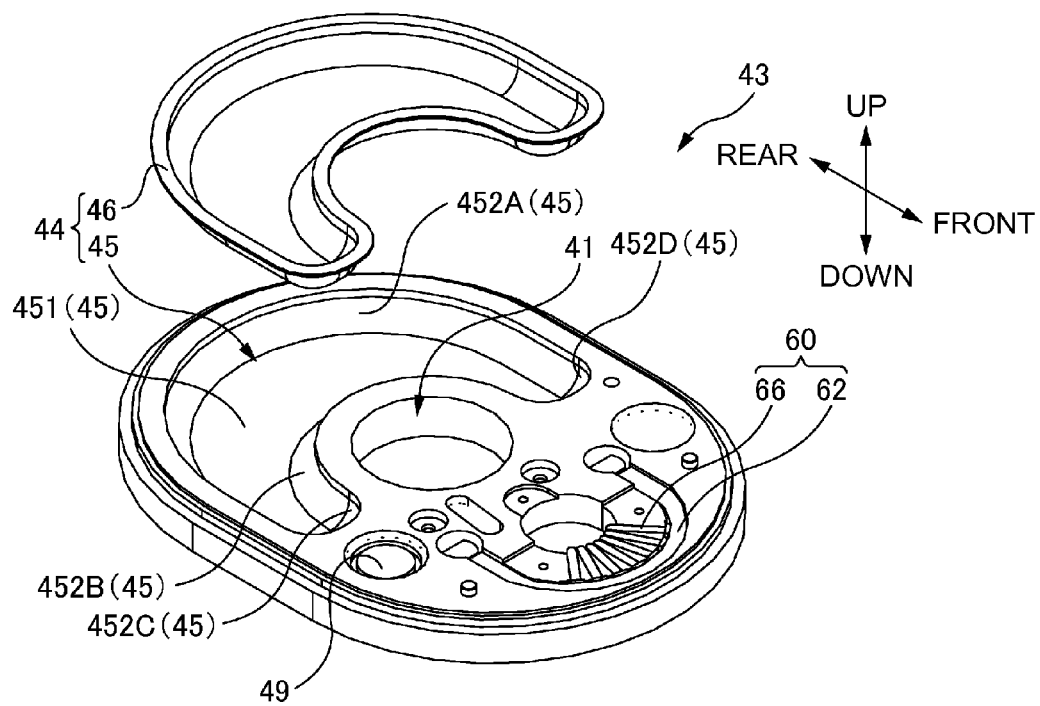
FIG. 8A is an exploded view of a reservoir.
Figure 8B:
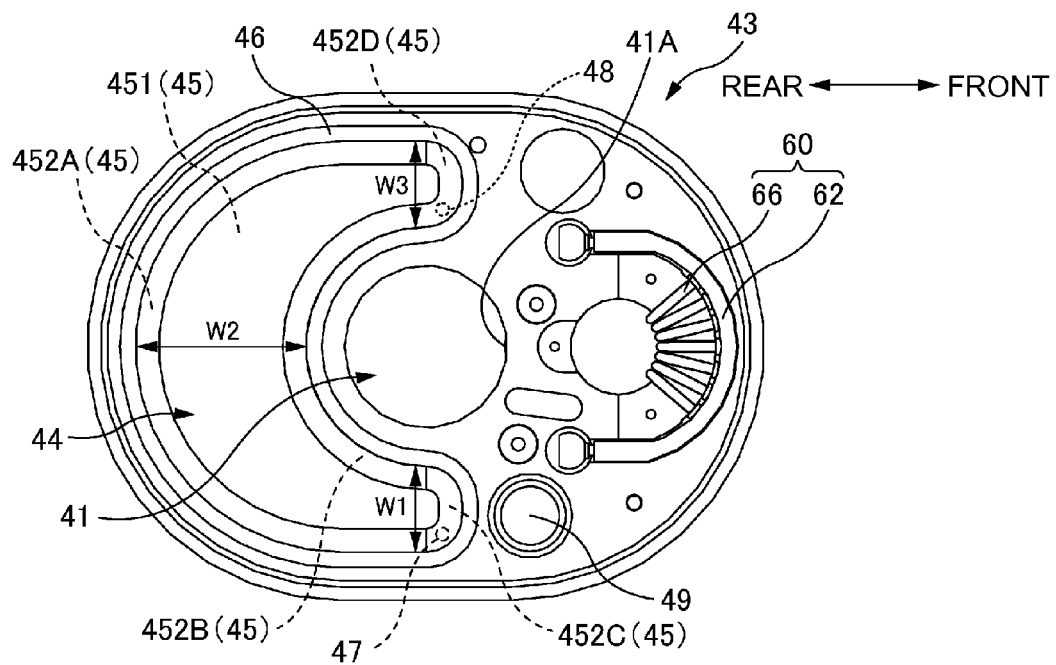
FIG. 8B is a top view of a cartridge main body.

FIG. 8A is an exploded view of a reservoir 44, and FIG. 8B is a top view of a cartridge main body 43.

The cartridge 40 includes the reservoir 44 (the storage portion) for storing the liquid. A concavity 45 is formed on the cartridge main body 43, and a film 46 is fused to the periphery of the concavity 45. The reservoir 44 is configured to have the concavity 45 and the film 46. The liquid is stored between the concavity 45 and the film 46. Meanwhile, in a state in FIG. 7, the film 46 is adhered to the concavity 45 and there is no liquid in the reservoir 44.

The concavity 45 is formed into a recessed shape from the upper surface of the cartridge main body 43 by bottom 451 and periphery 452. The bottom 451 of the concavity 45 is flat whereas the periphery 452 of the concavity 45 is curved. Meanwhile, in the same way, in the case of the film 46 (film 46 in a state where there is no liquid in the reservoir 44) which is adhered to the concavity 45, the bottom is flat whereas the periphery is curved. The periphery 452 of the concavity 45 is configured to have, as will be described later; an outer periphery 452A, an inner periphery 452B, a periphery on an injection side 452C, and a periphery on a discharge side 452D, and these surround the concavity 45.

The reservoir 44 is formed, when viewed from above, into a circular arc shape (alternatively a bow shape, a crescent shape, an oxbow lake shape, or a U shape) having the certain width. The outer periphery 452A of the reservoir 44 having the circular arc shape is disposed on the rear side of the pump and is formed into the circular arc shape which swells outside the reservoir 44 when viewed from above. The inner periphery 452B of the reservoir 44 having the circular arc shape is disposed so as to surround a half rear side of the receiving portion 41 (to avoid), and is formed into the circular arc shape which swells inside the reservoir 44 when viewed from above. The outer periphery 452A is more gently curved than the inner periphery 452B when viewed from above. That is, a curvature of the outer periphery 452A is smaller than a curvature of the inner periphery 452B, the radius of the curvature of the outer periphery 452A is larger than the radius of the curvature of the inner periphery 452B.

An injection port 47 which injects the liquid into the reservoir 44 is provided at one end of the reservoir 44 having the circular arc shape, and a discharge port 48 which discharges the liquid from the reservoir 44 is provided at the other end of the reservoir 44.

The injection port 47 is formed on the periphery on the injection side 452C which connects the outer periphery 452A and the inner periphery 452B. The injection port 47 is disposed to be close to the outside of the periphery on the injection side 452C. That is, the injection port 47 is disposed to be close to the outer periphery 452A side in the periphery on the injection side 452C. Accordingly, as will be described later, when the liquid starts to be injected into the reservoir 44, the liquid easily enters into the reservoir 44 along the outer periphery 452A (refer to FIGS. 9A and 9B).

The discharge port 48 is formed on the periphery on the discharge side 452D which connects the outer periphery 452A and the inner periphery 452B. The discharge port 48 is positioned at the end of the reservoir 44 having the circular arc shape. Accordingly, as will be described later, when the liquid is injected into the reservoir 44, the gas is not likely to remain in the reservoir 44.

Further, the discharge port 48 is disposed to be close to the inside of the periphery on the discharge side 452D. That is, the discharge port 48 is disposed to be close to the inner periphery 452B in the periphery on the discharge side 452D. Accordingly, as will be described later, when the liquid is injected to the reservoir 44, the gas is not likely to remain in the reservoir 44 (refer to FIG. 9C), and when the liquid of the reservoir 44 is discharged, the liquid is not likely to remain in the reservoir 44 (refer to FIG. 10B).

As illustrated in FIG. 8B, width W2 of the center portion in the reservoir 44 having the circular arc shape is greater than width W1 (the width between the outer periphery 452A and the inner periphery 452B of the periphery on the injection side 452C) of the periphery on the injection side 452C. In addition, the width W2 of the center portion in the reservoir 44 having the circular arc shape is greater than width W3 (the width between the outer periphery 452A and the inner periphery 452B of the periphery on the discharge side 452D) of the periphery on the discharge side 452D. Accordingly, the capacity of the reservoir 44 can be increased, and the film 46 of the center portion in the reservoir 44 is easily deformed.

The user punctures a septum for injection 49 of the cartridge 40 in a state of FIG. 7 (a state where there is no liquid in the reservoir 44) with an injector, and the liquid (for example, insulin) is injected into the reservoir 44 by using the injector. When the liquid is injected into the reservoir 44, the film 46 swells upward and the liquid is stored between the concavity 45 and the film 46.

FIGS. 9A to 9D are explanatory diagrams illustrating a state of the reservoir 44 when the liquid is injected from the injection port 47. A hatched region in the reservoir 44 in FIGS. 9A to 9D represents a region into which the liquid enters (penetrates). In addition, a region which is not hatched in the reservoir 44 represents a region without the liquid and represents a region in which the concavity 45 and the film 46 are adhered to each other.

Figure 9A:
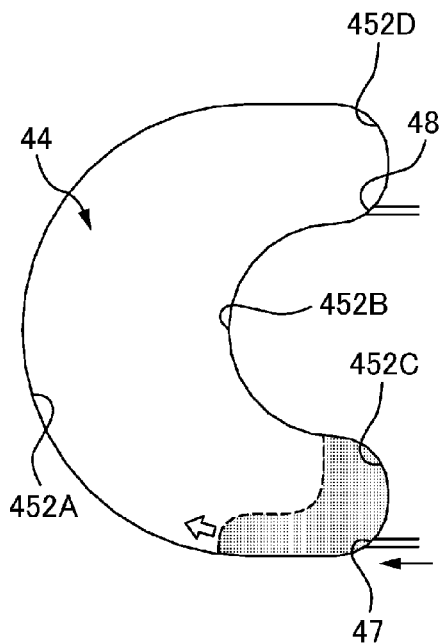
FIGS. 9A to 9D are explanatory diagrams illustrating a state of the reservoir when the liquid is injected from an injection port.

When the liquid starts to be injected into the reservoir 44 from the injection port 47 in a state of having no liquid therein, as illustrated in FIG. 9A, the liquid enters into the region in the vicinity of a certain periphery on the injection side 452C of the injection port 47. Moreover, when continuously injecting the liquid, as illustrated by a white arrow in FIG. 9A, the liquid enters into the reservoir 44 along the outer periphery 452A, thereby entering a state illustrated in FIG. 9B. The reason for the liquid to enter along the outer periphery 452A rather than the inner periphery 452B is that the outer periphery 452A is more gently curved than the inner periphery 452B, and thus the film 46 which is adhered to the outer periphery 452A is easily deformed compared to the film 46 which is adhered to the inner periphery 452B. Additionally, in the embodiment, since the injection port 47 is disposed to be close to the outside, the liquid more easily enters into the reservoir 44 along the outer periphery 452A.

In addition, in the embodiment, since the width (the width W2 in FIG. 8B) of the center portion in the reservoir 44 is large and thus the film 46 of the center portion in the reservoir 44 is easily deformed, the liquid which enters into the reservoir 44 along the outer periphery 452A is easily expanded in the center portion of the reservoir 44.

Figure 9B:
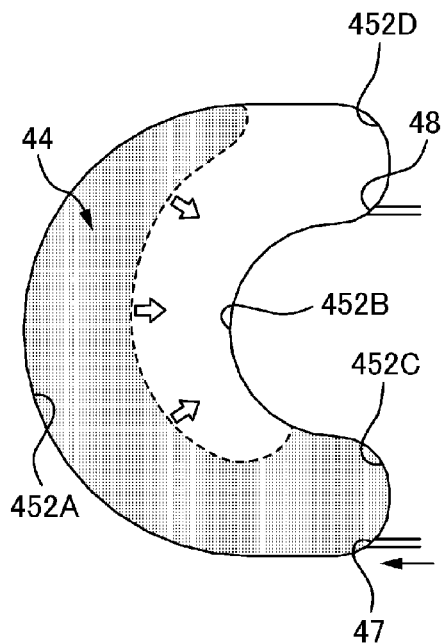

After the liquid enters along the outer periphery 452A, when the liquid is continuously injected, as illustrated by the white arrow in FIG. 9B, the liquid enters into the inner periphery 452B. In this manner, since the liquid sequentially enters into the inner periphery 452B after the liquid enters along the outer periphery 452A, even if the gas exists in the reservoir 44 before injecting the liquid, the gas moves to the inner periphery 452B, and thereby the gas is not likely to remain in the reservoir 44 (the gas is discharged from the discharge port 48 at the end).

Figure 9C:
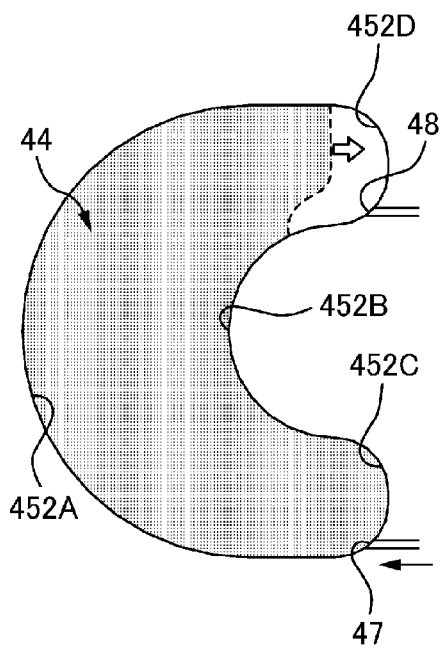

Further, when the liquid is continuously injected, as illustrated in FIG. 9C, the liquid enters into the region in the vicinity of the periphery on the discharge side 452D at the end. As described above, the film 46 of the outer periphery 452A is more easily deformed compared to the film 46 of the inner periphery 452B, and thus the liquid enters from the outer periphery 452A even when the liquid enters into the region in the vicinity of the periphery on the discharge side 452D, (refer to the white arrow in FIG. 9C). In the embodiment, since the discharge port 48 is disposed to be close to the inside, the gas is pushed out from the discharge port 48 and thus the gas is not likely to remain in the reservoir 44 even if the gas exists in the vicinity of the periphery on the discharge side 452D before injecting the liquid.

Meanwhile, in the embodiment, the injection port 47 is disposed at one end of the reservoir 44 having the circular arc shape, and the discharge port 48 is disposed at the other end on the opposite side. For this reason, when the liquid is injected from the injection port 47, the liquid enters into each region of the reservoir 44 having the circular arc shape and then the liquid enters into the side of the discharge port 48 at the end. For this reason, the gas moves to the discharge port 48, and the gas is not likely to remain in the reservoir 44 even in a case where the gas exists in the reservoir 44 before injecting the liquid.

Figure 9D:
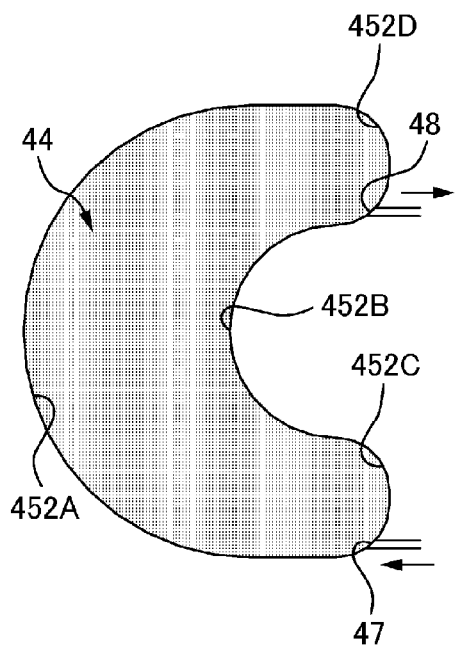

As illustrated in FIG. 9D, after the liquid enters into a surface between the concavity 45 and the film 46, if the user further injects the liquid, the liquid is pushed out from the discharge port 48 and thus a flow path to the liquid feeding port 41A is filled with the liquid. Note that since the septum for injection 49 is disposed on the upper side of the cartridge 40, it is not possible to attach the driving unit 31 to the cartridge 40 at the time of injecting the liquid. For this reason, since the tube 62 is not blocked at the time of injecting the liquid (a state where the cam 65 is not in the cam accommodation portion 42, and the tube 62 is not blocked by the finger 66), the flow path to the liquid feeding port 41A can be filled with the liquid.

Figure 13A:
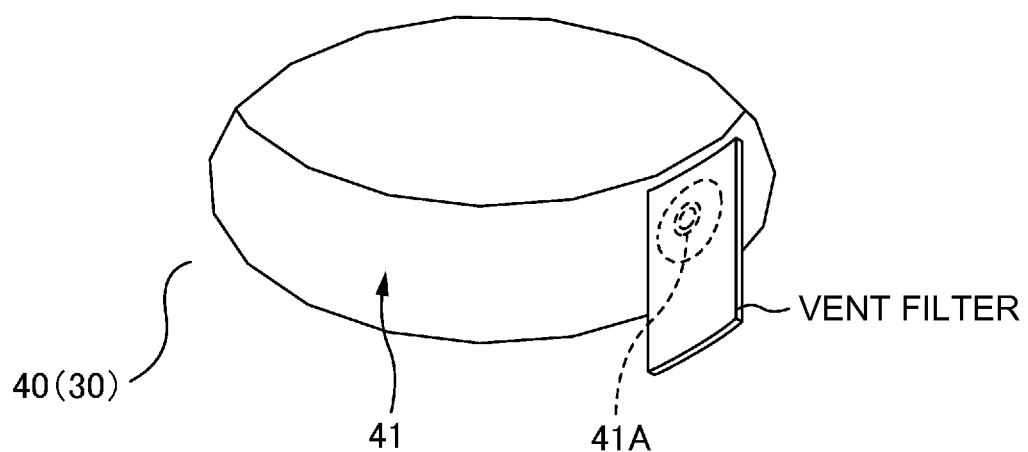
FIG. 13A is a perspective view of a vent filter which is attached to a liquid feeding port.

A vent filter (refer to FIG. 13A) is attached to the liquid feeding port 41A in advance at the time of injecting the liquid. The vent filter is a filter through which the gas can pass, but the liquid cannot pass. At the time of injecting the liquid, the gas in the flow path passes through the vent filter and is pushed out to the outside before the liquid reaches the liquid feeding port 41A. In addition, at the time of injecting the liquid, when the liquid which is discharged from the discharge port 48 reaches the liquid feeding port 41A, it is possible to prevent the liquid from leaking to the outside by the vent filter. In this stage, if the user further injects the liquid, the liquid pressure in the reservoir 44 is increased and the film 46 of the reservoir 44 swells upward, the liquid is further injected between the concavity 45 and the film 46, and thus a sufficient amount of the liquid can be stored in the reservoir 44. After injecting the liquid into the reservoir 44, the user detaches the vent filter from the liquid feeding port 41A (refer to FIG. 13B), and then inserts the pump unit 30 into the injection set.

Meanwhile, if the liquid is injected without the vent filter, since the liquid leaks to the outside from the liquid feeding port 41A, and the liquid pressure in the reservoir 44 is not increased, it is not possible to sufficiently store the liquid in the reservoir 44. Here, in a case where the resistance in the flow path is large, the liquid is stored in the reservoir 44 before the liquid reaches the liquid feeding port 41A, and thus the vent filter is not necessary in this state.

Figure 10A:
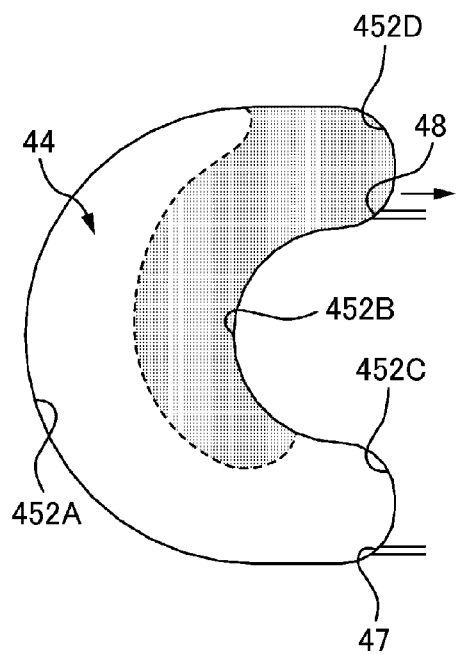
FIGS. 10A and 10B are explanatory diagrams illustrating a state when the liquid in the reservoir is discharged by the pumping portion.
Figure 10B:
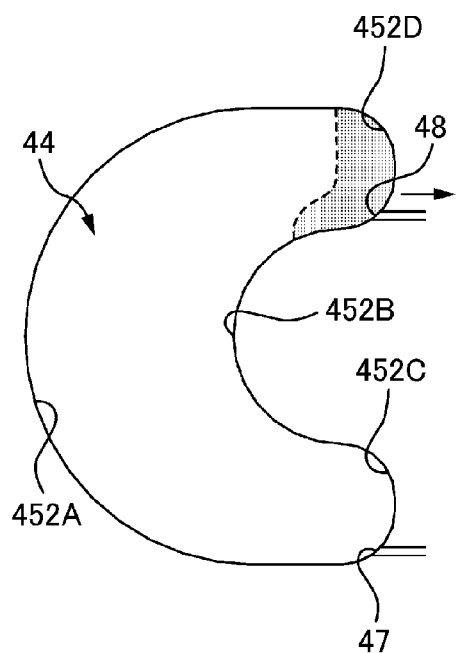

FIGS. 10A and 10B are explanatory diagrams illustrating a state when the liquid in the reservoir 44 is discharged by the pumping portion 60.

If the liquid in the reservoir 44 is continuously discharged by the pumping portion 60, the amount of the liquid in the reservoir 44 is decreased, and the concavity 45 and the film 46 of the reservoir 44 start to adhere to each other. As described above, since the film 46 of the outer periphery 452A is more easily deformed compared to the film 46 of the inner periphery 452B, as illustrated in FIG. 10A, the film 46 from the outer periphery 452A starts to be adhered to the concavity 45 in advance. Even after the film 46 of the outer periphery 452A is adhered to the concavity 45, the film 46 of the inner periphery 452B is not adhered to the concavity 45, and thus the liquid in the reservoir 44 is not likely to remain. If the film 46 is adhered to the concavity 45 at the center portion in the reservoir 44 in advance in a state where the liquid remains in the vicinity of the injection port 47, the liquid remains while the liquid cannot be discharged. However, in the embodiment, since the film 46 of the inner periphery 452B is not easily deformed and is not adhered to the concavity 45 as illustrated in FIG. 10A, the liquid in the vicinity of the injection port 47 passes through the vicinity of the inner periphery 452B and thus is discharged from the discharge port 48 through the shortest route.

Further, if the liquid is continuously discharged, the liquid in the vicinity of the periphery on the discharge side 452D remains at the end as illustrated in FIG. 10B. As described above, since the film 46 of the outer periphery 452A is more easily deformed compared to the film 46 of the inner periphery 452B, the liquid from the outer periphery 452A is discharged first. In the embodiment, the discharge port 48 is disposed to be close to the inside, and thus the liquid is not likely to remain in the reservoir 44.

Disposition of Catheter 12

Figure 11A:
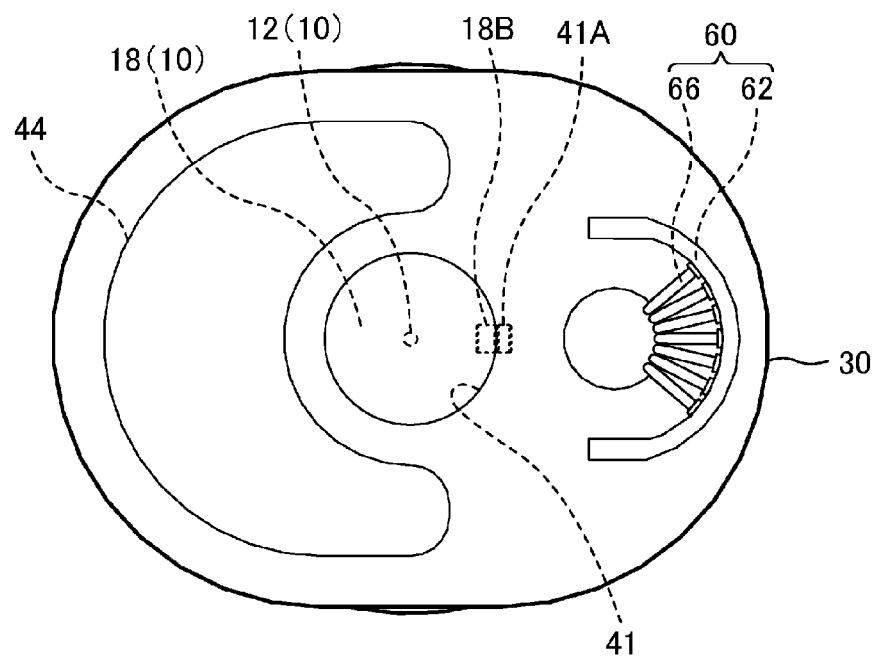
FIG. 11A is an explanatory diagram of a positional relationship between the pumping portion, the reservoir, and the catheter when viewing the liquid transport device from above.

FIG. 11A is an explanatory diagram of the positional relationship between the pumping portion 60, the reservoir 44, and the catheter 12 when viewing the liquid transport device 1 from above. For convenience of explanation, some components of the liquid transport device 1 are illustrated in perspective views.

As illustrated in FIG. 11A, when viewing the liquid transport device 1 from above (when viewed from the direction perpendicular to the surface of the living body), the catheter 12 and the liquid feeding port 41A are disposed between the reservoir 44 and the tube 62 (the pumping portion 60). As such, the catheter 12 and the liquid feeding port 41A are disposed, and thus the catheter 12 and the liquid feeding port 41A do not necessarily have to be disposed so as to protrude from the pump unit 30, therefore realizing the reduction of the size of the liquid transport device 1.

Figure 12:
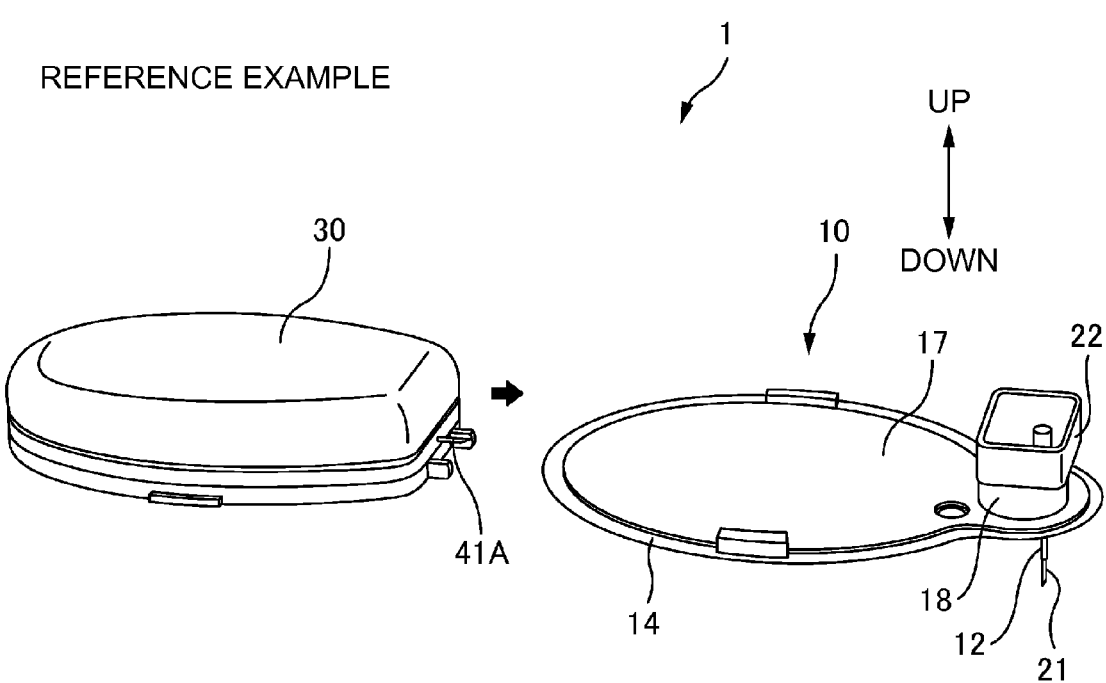
FIG. 12 is an explanatory diagram of a liquid transport device in a reference example.

FIG. 12 is an explanatory diagram of a liquid transport device 1 in a reference example. Although not shown, the reservoir 44 and the tube 62 (the pumping portion 60) are provided in the inside of the pump unit 30 in the reference example. In addition, in the reference example, the catheter 12 and the liquid feeding port 41A are provided on the outside of the pump unit 30 which includes the reservoir 44 and the tube 62 when viewing the liquid transport device 1 from above. For this reason, in the reference example, the catheter 12 and the liquid feeding port 41A are necessarily disposed to protrude from the pump unit 30, and thus the size of the liquid transport device 1 is increased. Meanwhile, even though the catheter 12 and the liquid feeding port 41A are disposed on the outside of the pump unit 30 as in the reference example, as long as a gap G is present between the pump unit 30 and the seal portion 14 (refer to FIG. 14) as will be described later, the liquid transport device 1 is easily fixed to the flexible surface of the living body, thereby reducing the load on the living body.

In the embodiment, the reservoir 44 is formed into the circular arc shape (the U shape), and the tube 62 is formed into the circular arc shape (the U shape) as well. In addition, the end portion (the discharge port 48) of the reservoir 44 having the circular arc shape is directed to the tube 62, and the end portion of the tube 62 having the circular arc shape is directed to the reservoir 44. For this reason, it is possible to shorten the flow path from the discharge port 48 of the reservoir 44 to the end on the upstream of the tube 62 and to shorten the flow path from the end on the downstream of the tube 62 to the liquid feeding port 41A.

In addition, in the embodiment, the reservoir 44 and the tube 62 are disposed such that the end portions having the circular arc shape (the U shape) face each other. Accordingly, the receiving portion 41 having a hollow shape is easily formed between the two members. Then, as in the embodiment, if the receiving portion 41 and the liquid feeding port 41A are disposed on the inside of the region (the region surrounded by the two members) surrounded by a line which connects the end portions of the reservoir 44, the tube 62, and the reservoir 44 and the end portion of the tube 62, it is possible to realize the reduction of the size of the liquid transport device 1. If the liquid feeding port 41A is disposed on the inside of a region which is formed into a rectangular shape and connects four end portions of the reservoir 44 and the tube 62, it is possible to realize the reduction of the size of the pump unit 30.

In addition, in the embodiment, curved portions of the two members having the circular arc shape (the reservoir and the tube 62) are disposed to face the outside. Accordingly, the pump unit 30 (or the cartridge 40) accommodating the two members is easily reduced in size.

Figure 11B:
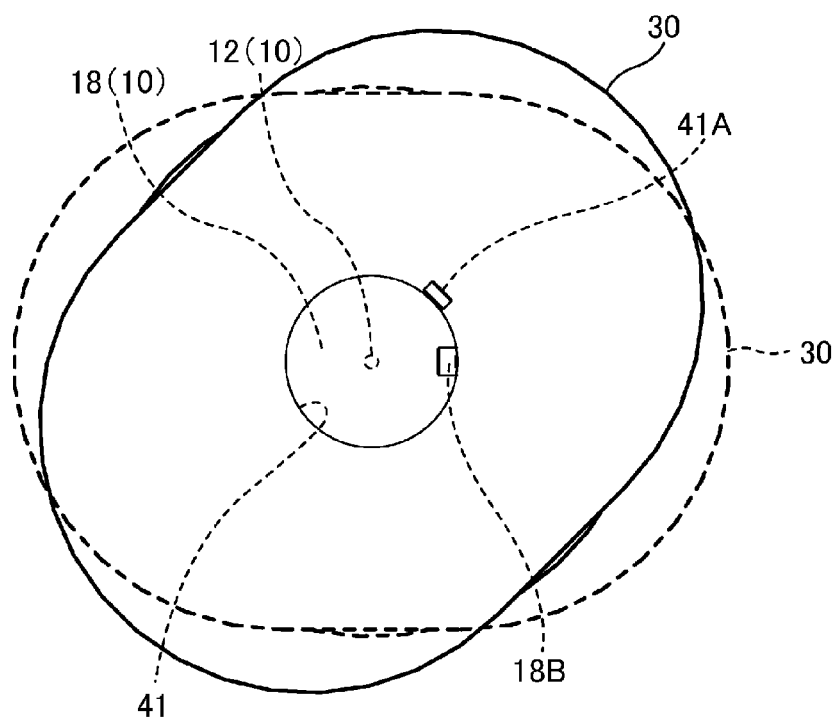
FIG. 11B is an explanatory diagram illustrating the movement of the pump unit at the time of being mounted in the injection set.

FIG. 11B is an explanatory diagram illustrating the movement of the pump unit 30 at the time of being mounted on the injection set. The user inserts the connection portion 18 of the injection set 10 into the receiving portion 41 of the pump unit 30, and then mounts the pump unit 30 on the injection set 10 while rotating the pump unit 30 in the axial direction perpendicular to the surface of the living body as illustrated in FIG. 11B. A stopper (not shown) is formed in at least one of the connection portion 18 of the injection set 10 and the receiving portion 41 of the pump unit 30 so that the rotation of the pump unit 30 stops at a position in which the liquid receiving port 18A of the injection set 10 and the liquid feeding port 41A of the pump unit 30 face to each other.

In the embodiment, as described above, since the catheter 12 and the liquid feeding port 41A are disposed between the reservoir 44 and the tube 62 (the pumping portion 60), the catheter 12 is positioned in the vicinity of the rotation center of the pump unit 30. For this reason, as illustrated in FIG. 11B, when the pump unit 30 is mounted on the injection set 10 while being rotated, the load (pain) on the living body from the catheter 12 is small even though torque of the pump unit 30 is transferred to the injection set 10.

Figure 13B:
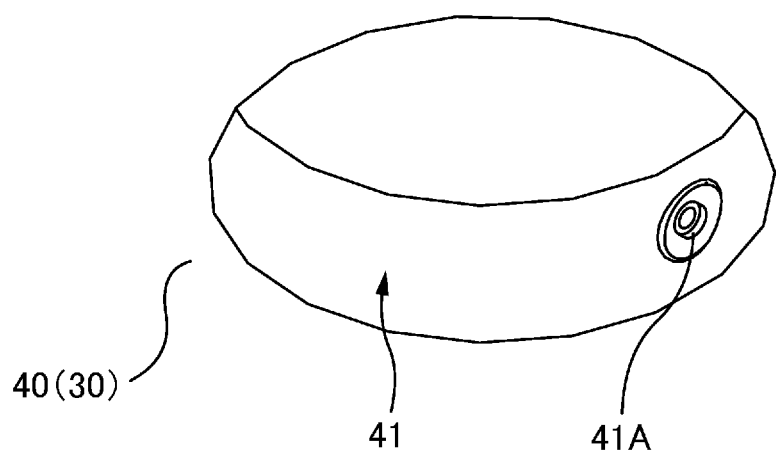
FIG. 13B is a perspective view of the liquid feeding port of a receiving portion of the pump unit.

FIG. 13B is a perspective view of the liquid feeding port 41A of a receiving portion 41 of the pump unit 30. The liquid feeding port 41A is formed of an elastically deformable rubber and is configured to protrude inward from the inner circumferential surface of the receiving portion 41 (in other words, protruding toward the connection portion 18 of the injection set 10). On the other hand, the liquid receiving port 18A of the injection set 10 (refer to FIG. 3A) is also formed from the elastically deformable rubber, and is configured to protrude outward from the side surface of the connection portion 18 (in other words, protruding toward the inner circumferential surface of the receiving portion 41 of the pump unit 30). When the pump unit 30 is mounted on the injection set 10, the liquid feeding port 41A and the liquid receiving port 18A are connected to each other. At this time, the liquid feeding port 41A and the liquid receiving port 18A which protrude are connected to each other while being elastically deformed, and thus are connected without a gap therebetween.

Fixing Method of Pump Unit 30

In the case of the liquid transport device 1 in the reference example as illustrated in FIG. 12, the seal portion 14 is fixed to the entire lower surface of the pump unit 30. However, in the case of the reference example, since the lower surface (the sealing surface) of the seal portion 14 is formed into a planar shape, the liquid transport device 1 is easily detached from the flexible surface of the living body, or the surface of the living body is corrected to be formed into a planar shape by the flat sealing surface, and thereby the load (pain) on the living body is increased.

On the other hand, the pump unit 30 needs to be large enough that the pumping portion 60 and the reservoir 44 can be accommodated therein and thus there is a limitation to the reduction of an area of the lower surface of the pump unit 30. In addition, the sealing surface of the seal portion 14 also needs to have a large enough area that the liquid transport device 1 can be fixed to the surface of the living body, and thus there is a limitation to the reduction of the seal portion 14.

Thus, in the embodiment, as described below, by disposing the lower surface of the pump unit 30 to be floated from the seal portion 14, the pump unit 30 is easily fixed to the flexible surface of the living body and a load on the living body is reduced while securing areas for the lower surface of the pump unit 30 and the sealing surface of the seal portion 14.

As illustrated in FIG. 3A, the base portion 17 of the embodiment is configured as a disk shaped part which is smaller than the disk shaped seal portion 14. For this reason, the sealing surface of the seal portion 14 extends outward not only from the lower side of the base portion 17, but also from the outer circumference of the base portion 17. In addition, the base portion 17 is configured so that the upper surface of the base portion 17 is narrower than the lower surface of the pump unit 30. For this reason, if the pump unit 30 is supported on the base portion 17, a portion of the pump unit 30 protrudes from the base portion 17 (will be described later; refer to FIG. 14).

The sealing surface immediately below the base portion 17 is formed into a solid planar shape according to the lower surface of the base portion 17. For this reason, when attaching the seal portion 14 to the surface of the living body, the surface of the living body is corrected so as to be a planar surface by the sealing surface of the lower side of the base portion 17. Here, since the area of the base portion 17 is small compared to the entire area of the seal portion 14, the region in which the surface of the living body is corrected to be planar surface is small and thereby the load (pain) on the living body is reduced.

The sealing surface which extends to the outside from the outer circumference of the base portion 17 causes the area of the sealing surface of the seal portion 14 to extend to the extent that the liquid transport device 1 is fixed to the living body. The sealing surface of the region is not fixed in the planar shape by the base portion 17, has flexibility, and thus can be deformed along the surface of the living body. For this reason, the sealing surface of the region is not easily detached from the flexible surface of the living body and thereby the load on the living body is reduced.

Figure 14:
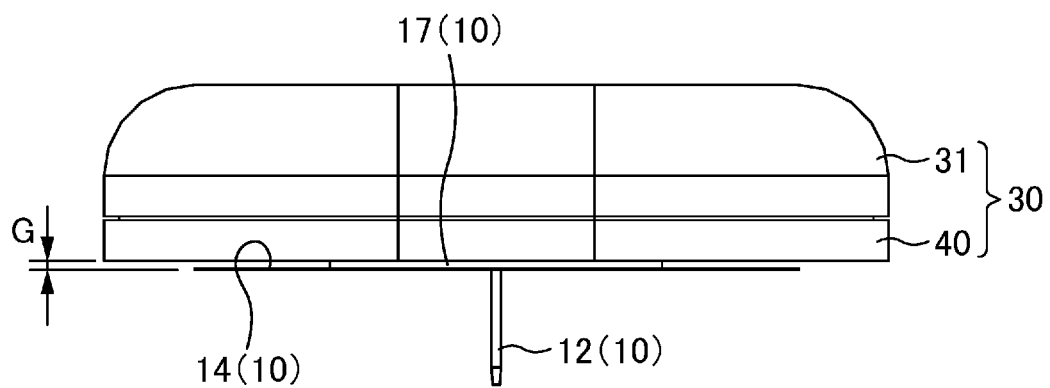
FIG. 14 is a side view of the liquid transport device.

FIG. 14 is a side view of the liquid transport device 1.

When the pump unit 30 is mounted on the injection set 10, the lower surface of the pump unit 30 comes in contact with the upper surface of the base portion 17 (refer to FIG. 3A) of the injection set 10, and the pump unit 30 is supported by the base portion 17 of the injection set 10. As a result, as illustrated in FIG. 14, a portion of the pump unit 30 protrudes from the base portion 17. The base portion 17 has a predetermined thickness, and the gap G is generated by this thickness between a portion of the lower surface of the pump unit 30 (a portion protruding from the base portion 17) and the upper surface of the seal portion 14. That is, a portion of the lower surface of the pump unit 30 is far from the upper surface of the seal portion 14 (state of being floated from the seal portion 14).

Since the gap G is present between the pump unit 30 and the seal portion 14, even after the pump unit 30 is mounted on the injection set 10, the sealing surface which extends to the outside from the outer circumference of the base portion 17 is not fixed in the planar shape by the lower surface of the pump unit 30, can continuously maintain flexibility, and thus can be deformed along the surface of the living body. For this reason, even after the pump unit 30 is mounted on the injection set 10, the liquid transport device 1 is not easily detached from the flexible surface of the living body, and thus the load on the living body is reduced.

In addition, as illustrated in FIG. 14, the pump unit 30 further protrudes from the upper surface of the seal portion 14. In other words, the seal portion 14 can be configured to be smaller than the lower surface of the pump unit 30. In the aforementioned reference example, the seal portion 14 corresponding to the area of the lower surface of the pump unit 30 is attached to the living body, but in contrast, in the embodiment, the seal portion 14 can be made to be smaller than the area of the lower surface of the pump unit 30, and thereby the load on the living body can be reduced.

In addition, in the embodiment, the pump unit 30 is detachably provided with respect to the injection set 10. Accordingly, the pump unit 30 can be detached from the injection set 10 in a state where the living body is punctured with the catheter 12, and thus it is convenient that, for example, the cartridge 40 can be exchanged or the liquid can be re-injected into the reservoir 44.

Further, in the embodiment, the sealing surface of the seal portion 14 is disposed on the periphery of the catheter 12. Accordingly, when the injection set 10 is attached to the living body, since the periphery of the catheter 12 is fixed to the living body through the seal portion 14, the catheter 12 is not easily detached. Further, in the embodiment, the seal portion 14 on the periphery of the catheter 12 is positioned on the lower side of the base portion 17. For this reason, the surface of the living body does not easily move on the periphery of the catheter 12, and thus it is possible to reduce the load on the living body from the catheter 12.

Meanwhile, in the first embodiment, as illustrated in FIG. 11A, when viewed from above (when viewed from the direction perpendicular to the surface of the living body to which the liquid transport device 1 is attached), the catheter 12 is disposed between the reservoir 44 and the tube 62. Note that the disposition of the catheter 12, the reservoir 44, and the tube 62 is not limited to the above description. For example, when viewed from above (when viewed from the direction perpendicular to the surface of the living body to which the liquid transport device 1 is attached), the tube 62 may be disposed between the reservoir 44 and the catheter 12. Even in this case, as long as the gap G is present between the pump unit 30 and the seal portion 14 (refer to FIG. 14), the liquid transport device 1 is easily fixed to the flexible surface of the living body, and thus it is possible to reduce the load on the living body.

Here, the shape of the reservoir 44 (the storage portion) of the embodiment will be described.

As illustrated in FIG. 8B, the reservoir 44 (the storage portion) of the embodiment is formed into the circular arc shape having the certain width. In a case where the reservoir 44 is assumed to be the circular arc shape having the certain width, the outer periphery 452A which swells outside the reservoir 44 and the inner periphery 452B which swells inside the reservoir 44 are formed. Meanwhile, in a case where the reservoir 44 is assumed to be the circular arc shape, since the inner periphery 452B can be disposed to avoid the receiving portion 41, the reservoir 44 having a large capacity can be formed in a narrow area. Further, in the embodiment, the discharge port 48 is disposed at one end of the reservoir 44 having such a shape. Accordingly, as illustrated in FIGS. 10A and 10B, even in a case where the concavity 45 and the film 46 of the reservoir 44 start to adhere to each other at the time of discharging the liquid, since the film 46 of the inner periphery 452B is not easily adhered to the concavity 45, the liquid in the reservoir 44 passes through the vicinity of the inner periphery 452B as the flow path and is discharged from the discharge port 48. For this reason, according to the embodiment, the liquid is not likely to remain in the reservoir 44 at the time of discharging the liquid, and thus it is possible to efficiently use the liquid in the reservoir 44.

In addition, in the embodiment, the discharge port 48 is disposed to be close to the inside of the periphery on the discharge side 452D (a position which is closer to the inner periphery 452B than the outer periphery 452A). Accordingly, when the liquid is injected into the reservoir 44, the gas is not likely to remain in the reservoir 44 (refer to FIG. 9C), and when the liquid in the reservoir 44 is discharged, the liquid is not likely to remain in the reservoir 44 (refer to FIG. 10B).

In addition, in the embodiment, the injection port 47 is disposed at the other end on the side opposite to the discharge port 48. By disposing the injection port 47 and the discharge port 48 as described above, the gas is moved to the discharge port 48 and then discharged from the discharge port 48 at the time of injecting the liquid, and thus the gas is not likely to remain in the reservoir 44 even if the gas exists in the reservoir 44 before injecting the liquid.

In addition, in the embodiment, the injection port 47 is disposed to be close to the outside of the periphery on the injection side 452C (a position which is closer to the outer periphery 452A than the inner periphery 452B). Accordingly, when the liquid starts to be injected into the reservoir 44, the liquid easily enters into the reservoir 44 along the outer periphery 452A, the liquid sequentially enters into the respective regions in the reservoir 44, and thus the gas is not likely to remain in the reservoir 44.

Further, in the embodiment, the outer periphery 452A is more gently curved than the inner periphery 452B, and the curvature of the outer periphery 452A is smaller than the curvature of the inner periphery 452B. As a result, since the film 46 of the outer periphery 452A is more easily deformed compared to the film 46 of the inner periphery 452B and the liquid enters along the outer periphery 452A rather than the inner periphery 452B at the time of being injected, the liquid sequentially enters into the respective regions in the reservoir 44, and thus the gas is not likely to remain in the reservoir 44. In addition, since the liquid from the outer periphery 452A is sequentially discharged at the time of being discharged, the liquid is not likely to remain in the reservoir 44.

In addition, in the embodiment, as illustrated in FIG. 8B, the width W2 of the center portion in the reservoir 44 is larger than the widths W1, W3 of the end portion in the reservoir 44. Accordingly, the capacity of the reservoir 44 can be increased and the film 46 of the center portion in the reservoir 44 is easily deformed.

In addition, in the embodiment, when the liquid is injected into the reservoir 44, the vent filter is attached to the liquid feeding port 41A in advance. Accordingly, it is possible to prevent the liquid from leaking to the outside while discharging the gas in the flow path to the outside at the time of injecting the liquid. Further, it is possible to store a sufficient amount of the liquid in the reservoir 44 by increasing the liquid pressure in the reservoir 44.

Note that, in the first embodiment, as illustrated in FIG. 11A, when viewed from above (when viewed from the direction perpendicular to the surface of the living body to which the liquid transport device 1 is attached), the catheter 12 is disposed between the reservoir 44 and the tube 62. Here, the disposition of the catheter 12, the reservoir 44, and the tube 62 is not limited to the above description. For example, when viewed from above (when viewed from the direction perpendicular to the surface of the living body to which the liquid transport device 1 is attached), the tube 62 may be disposed between the reservoir 44 and the catheter 12. Even in this case, as long as the reservoir 44 is formed into the circular arc shape having the certain width and the discharge port 48 is disposed at one end of the reservoir 44 having the circular arc shape (refer to FIGS. 8A and 8B), the liquid is not likely to remain in the reservoir 44 at the time of being discharged, and thus it is possible to efficiently use the liquid in the reservoir 44.

Second Embodiment

In the aforementioned embodiment, the pumping portion 60 transports the liquid by compressing the tube 62 with the compression mechanism 64 which is configured to include the cam 65 and the finger 66. Here, the pumping portion 60 is not limited to the above described configuration.

Figure 15:
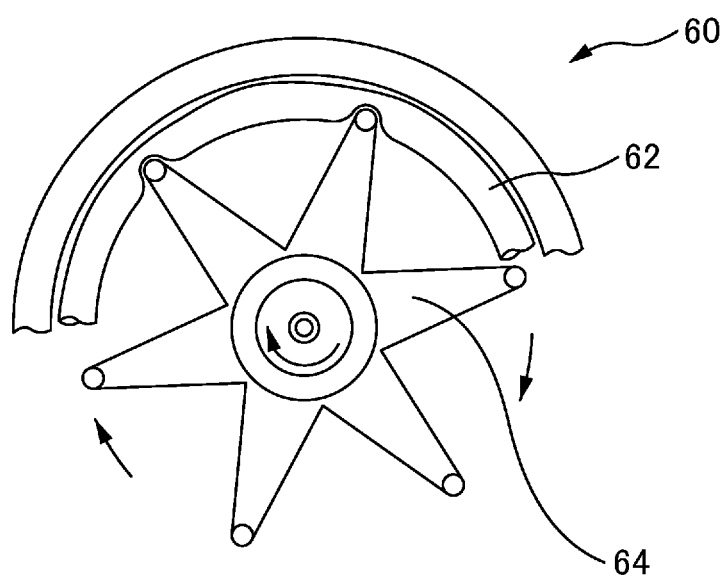
FIG. 15 is an overview diagram of a pumping portion in a second embodiment.

FIG. 15 is an overview diagram of the pumping portion 60 in the second embodiment. The compression mechanism 64 is configured to have rotatable members including a plurality of projection portions so as to block the tube 62. Also in a case where the pumping portion 60 is configured as described above, if a portion of the lower surface of the pump unit 30 is far from the upper surface of the seal portion 14 (state of being floated from the seal portion 14), the liquid transport device 1 is not easily detached from the flexible surface of the living body, and thus the load on the living body is reduced.

In addition, also in a case where the pumping portion 60 is configured as described above, if the reservoir 44 (not shown in FIG. 15) is configured to be the same as that in the aforementioned embodiment, the liquid is not likely to remain in the reservoir 44 at the time of being discharged, and thus it is possible to efficiently use the liquid in the reservoir 44.

Meanwhile, the pumping portion 60 is not limited to having the mechanism (the compression mechanism) for compressing the tube 62. For example, the pumping portion 60 may be a syringe pump for transporting the liquid by using a piston.

Third Embodiment

In the aforementioned embodiments, the pump unit 30 including the reservoir 44 and the pumping portion 60 is configured to be detachable with respect to the injection set 10. However, the pump unit 30 may be integrally formed by being fixed to the injection set 10.

Fourth Embodiment

Figure 16:
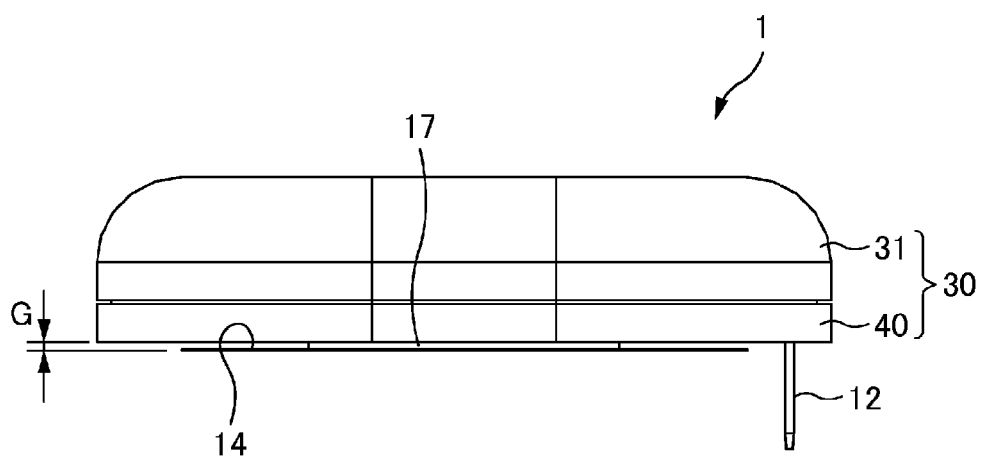
FIG. 16 is an explanatory diagram of a fourth embodiment.

FIG. 16 is an explanatory diagram of the fourth embodiment. The liquid transport device 1 of the fourth embodiment includes the pump unit 30 and the seal portion 14. The base portion 17 is fixed to the seal portion 14 and the pump unit 30 is fixed onto the base portion 17. That is, in the fourth embodiment, the pump unit 30 and the seal portion 14 are integrally formed via the base portion 17.

In the fourth embodiment, the catheter 12 is disposed on the lower surface of the pump unit 30. The catheter 12 is disposed on the lower surface of the pump unit 30 protruding from the seal portion 14 and is disposed on the outside of the seal portion 14.

In the fourth embodiment, as in the first embodiment, since the sealing surface of the seal portion 14 is not disposed on the periphery of the catheter 12, the catheter 12 is more easily moved compared to in the first embodiment, and thereby the load on the living body from the catheter 12 is possibly increased along with the catheter 12 being easily detached. On the other hand, also in a case where the liquid transport device 1 is configured as described above, since a portion of the lower surface of the pump unit 30 is far from the upper surface of the seal portion 14, the liquid transport device 1 is not easily detached from the flexible surface of the living body, and thus the load on the living body from the seal surface is reduced.

Meanwhile, in FIG. 16, the pump unit 30 and the seal portion 14 are integrally formed via the base portion 17, and the catheter 12 is disposed on the lower surface of the pump unit 30. Here, the pump unit 30 and the seal portion 14 may be integrally formed via the base portion 17, and the injection set 10 including the catheter 12 may be formed to be separate (detachably) from the pump unit 30. Even in this case, as long as a portion of the lower surface of the pump unit 30 is far from the upper surface of the seal portion 14, the liquid transport device 1 is not easily detached from the flexible surface of the living body, and thus the load on the living body from the seal surface is reduced.

Fifth Embodiment

Figure 17A:
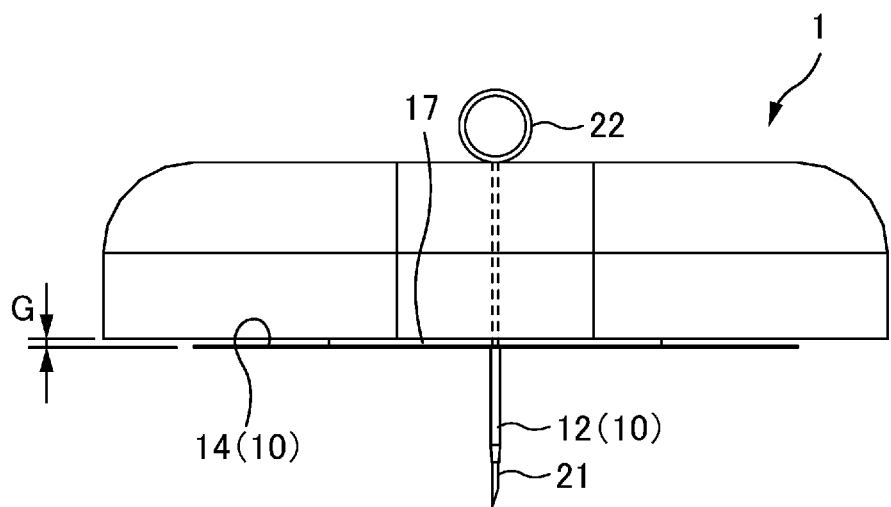
FIGS. 17A and 17B are explanatory diagrams of the liquid transport device before and after being attached to a living body in a fifth embodiment.
Figure 17B:
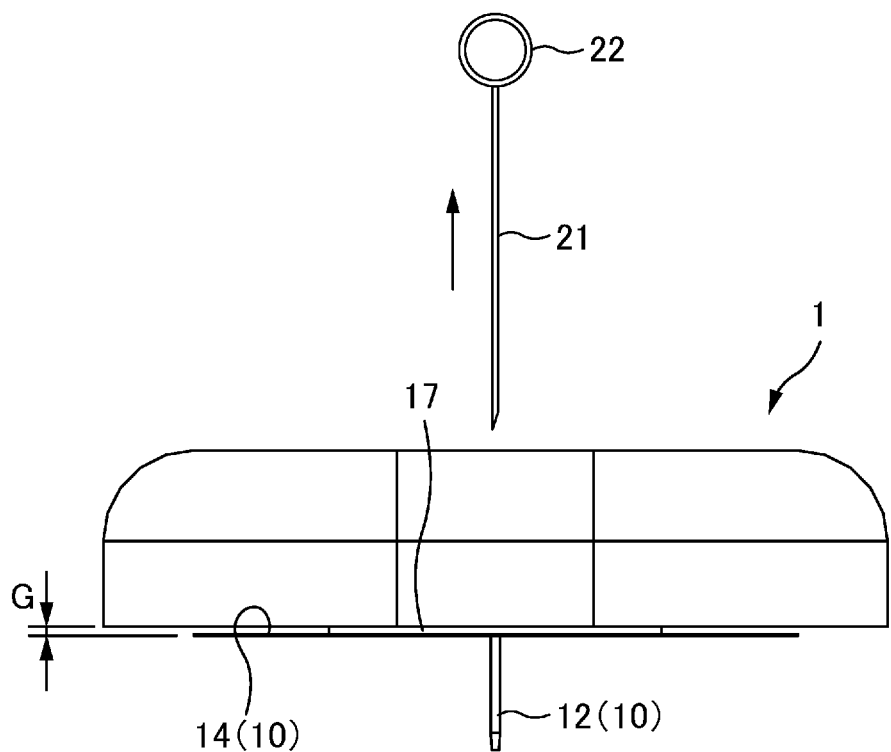

FIGS. 17A and 17B are explanatory diagrams of the liquid transport device 1 before and after being attached to the living body in the fifth embodiment. In the fourth embodiment, members corresponding to the aforementioned driving unit 31 and the cartridge 40 are integrally formed to configure the pump unit 30. In addition, in the fifth embodiment, the pump unit 30 is configured such that the seal portion 14 and the base portion 17 are integrally formed.

As illustrated in FIG. 17A, the introduction needle 21 is attached to the liquid transport device 1 before being attached, and the introduction needle 21 pierces through the entire liquid transport device 1 and a lower end of the introduction needle 21 protrudes from the lower side of the catheter 12. The user attaches the liquid transport device 1 to the living body while puncturing the living body with the catheter 12 together with the introduction needle 21. Thereafter, as illustrated in FIG. 17B, the user grabs the knob 22 of the introduction needle 21 in order to pull out the introduction needle 21 from the liquid transport device 1. A configuration may be adopted by which the living body is punctured with the combination of the introduction needle 21 and the catheter 12 through the liquid transport device 1 after the user attaches the liquid transport device 1 to the living body.

Also in the fifth embodiment, since a portion of the lower surface of the pump unit 30 is far from the upper surface of the seal portion 14, the liquid transport device 1 is not easily detached from the flexible surface of the living body, and thus the load on the living body from the seal surface is reduced.

Although not shown in FIGS. 17A and 17B, even in the fifth embodiment, as long as the reservoir 44 is formed into the circular arc shape having the certain width and the discharge port 48 is disposed at one end of the reservoir 44 having the circular arc shape, the liquid is not likely to remain in the reservoir 44 at the time of discharging the liquid, and thus it is possible to efficiently use the liquid in the reservoir 44.

Sixth Embodiment

Figure 18A:
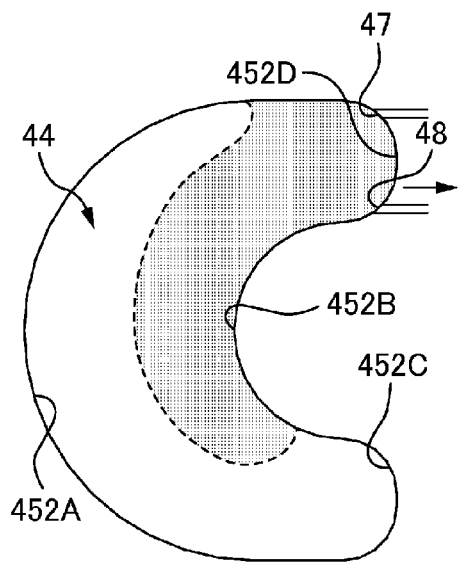
FIGS. 18A and 18B are explanatory diagrams of a reservoir in a sixth embodiment.
Figure 18B:
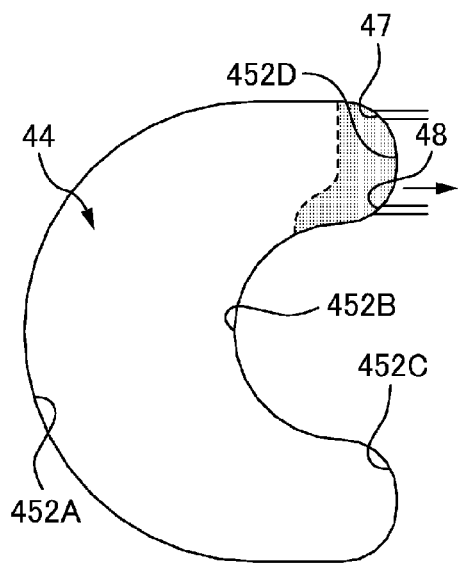

FIGS. 18A and 18B are explanatory diagrams of a reservoir in the sixth embodiment.

Also in the sixth embodiment, the reservoir 44 (the storage portion) is formed into the circular arc shape having the certain width and the discharge port 48 is disposed at one end of the reservoir 44. Accordingly, as illustrated in FIGS. 18A and 18B, even in a case where the concavity 45 and the film 46 of the reservoir 44 start to adhere to each other at the time of discharging the liquid, since the film 46 of the inner periphery 452B is not easily adhered to the concavity 45, the liquid in the reservoir 44 passes through the vicinity of the inner periphery 452B as the flow path and is discharged from the discharge port 48. For this reason, according to the embodiment, the liquid is not likely to remain in the reservoir 44 at the time of discharging the liquid, and thus it is possible to efficiently use the liquid in the reservoir 44.

In addition, also in the sixth embodiment, the discharge port 48 is disposed to be close to the inside of the periphery on the discharge side 452D (a position which is closer to the inner periphery 452B than the outer periphery 452A). Accordingly, when the liquid in the reservoir 44 is discharged, the liquid is not likely to remain in the reservoir 44 (refer to FIG. 16B).

On the other hand, in the sixth embodiment, the injection port 47 is provided at one end on the same side as the discharge port 48. For this reason, when the liquid is injected into the reservoir 44 from the injection port 47, the gas in the reservoir 44 is moved to the end portion on the side opposite to the discharge port and thus is not easily discharged from the discharge port 48. For this reason, in the sixth embodiment, the gas is more likely to remain in the reservoir 44 compared to the first embodiment.

Others

The above embodiments are intended to facilitate the understanding of the invention and are not intended to be construed as limiting the invention. The invention, without departing from the spirit thereof, may be modified or improved, and the invention of course includes equivalents thereof.

The entire disclosure of Japanese Patent Application Nos. 2014-44767, filed Mar. 7, 2014 and 2014-44768, filed Mar. 7, 2014 are expressly incorporated by reference herein.

What is claimed is:

1. A liquid transport device which is attachable to a living body and transports a liquid into the living body, the device comprising:
   a pump unit that includes a storage portion for storing the liquid and a pumping portion for transporting the liquid in the storage portion into the living body; and
   an adhesive seal portion that attaches the pump unit to the living body,
      wherein the pump unit is capable of being attached and detached from the seal portion and wherein a portion of a surface of the living body side of the pump unit is separated from an upper surface of the seal portion when the pump unit is attached to the seal portion such that an observable open air gap is formed between the seal portion and the pump unit when the liquid transport device is attached to the living body.

2. The liquid transport device according to claim 1, wherein a portion of the surface of the living body side of the pump unit protrudes in a direction along the surface of the living body from the seal portion.

3. The liquid transport device according to claim 1, wherein the pump unit is detachably provided in an injection set including the seal portion.

4. The liquid transport device according to claim 1, wherein the seal portion is disposed on the periphery of an injection portion for injecting the liquid which is transported by the pump unit to the living body.

5. The liquid transport device according to claim 4, wherein the pump unit is detachably provided with respect to the injection set including the seal portion and the injection portion,
wherein the injection set includes a pedestal portion supporting the pump unit, and
wherein the seal portion which is positioned under the pedestal portion is disposed on the periphery of the injection portion.

6. The liquid transport device according to claim 1, wherein the storage portion is formed into a circular arc shape having a width, and
wherein a discharge port for discharging the liquid in the storage portion to the pump unit is disposed at one end of the storage portion having the circular arc shape.

7. The liquid transport device according to claim 6, wherein the discharge port is disposed at a position which is closer to an inner periphery which swells inside and has the circular arc shape than an outer periphery which swells outside and has the circular arc shape.

8. The liquid transport device according to claim 7, wherein an injection port for injecting the liquid into the storage portion is disposed at the other end which is on the side opposite to the one end at which the discharge port of the storage portion having the circular arc shape is provided.

9. The liquid transport device according to claim 8, wherein the injection port is disposed at a position which is closer to the outer periphery than the inner periphery.

10. The liquid transport device according to claim 7, wherein the curvature of the outer periphery is smaller than the curvature of the inner periphery.

11. The liquid transport device according to claim 6, wherein the width in the center portion of the storage portion is greater than the width in the end portion of the storage portion.

12. The liquid transport device according to claim 6, further comprising:
   a liquid feeding port for sending the liquid transported by the pump unit to the outside,
   wherein a filter is provided in the feed liquid port, which allows a gas to pass through but does not allow the liquid to pass through at the time of injecting the liquid to the storage portion.

* * * * *